(12) United States Patent
Kemp et al.

(10) Patent No.: US 8,049,900 B2
(45) Date of Patent: Nov. 1, 2011

(54) APPARATUS AND METHODS FOR UNIFORM FREQUENCY SAMPLE CLOCKING

(75) Inventors: Nathaniel J. Kemp, Austin, TX (US); Roman Kuranov, Austin, TX (US); Austin Broderick McElroy, Austin, TX (US); Thomas E. Milner, Austin, TX (US)

(73) Assignee: Volcano Corporation, San Diego, CA (US)

( * ) Notice: Subject to any disclaimer, the term of this patent is extended or adjusted under 35 U.S.C. 154(b) by 442 days.

(21) Appl. No.: 12/172,980

(22) Filed: Jul. 14, 2008

(65) Prior Publication Data

US 2009/0046295 A1    Feb. 19, 2009

Related U.S. Application Data

(60) Provisional application No. 60/949,467, filed on Jul. 12, 2007.

(51) Int. Cl.
*G01B 11/02* (2006.01)
(52) U.S. Cl. ............................................. 356/497
(58) Field of Classification Search ............ 356/479, 356/497, 491; 250/339.07–339.09
See application file for complete search history.

(56) References Cited

U.S. PATENT DOCUMENTS

| | | | | |
|---|---|---|---|---|
| 4,803,639 A | 2/1989 | Steele et al. | ............... | 364/507 |
| 4,864,578 A | 9/1989 | Proffitt et al. | ............... | 372/20 |
| 4,969,742 A | 11/1990 | Falk et al. | ............... | 356/346 |
| 5,025,445 A | 6/1991 | Anderson et al. | ............... | 372/20 |
| 6,043,883 A | 3/2000 | Leckel et al. | ............... | 356/346 |
| 6,538,778 B1 | 3/2003 | Leckel et al. | ............... | 359/110 |
| 6,570,894 B2 | 5/2003 | Anderson | ............... | 372/32 |
| 6,646,745 B2 | 11/2003 | Verma et al. | ............... | 356/450 |
| 6,795,188 B2 | 9/2004 | Ruck et al. | ............... | 356/416 |
| 6,795,196 B2 | 9/2004 | Funakawa | ............... | 356/450 |
| 6,798,522 B2 | 9/2004 | Stolte et al. | ............... | 356/477 |
| 6,912,051 B2 | 6/2005 | Jensen | ............... | 356/450 |
| 6,937,346 B2 | 8/2005 | Nebendahl et al. | ............... | 356/519 |
| 6,947,147 B2 | 9/2005 | Motamedi et al. | ............... | 356/479 |
| 6,985,234 B2 | 1/2006 | Anderson | ............... | 356/477 |

(Continued)

FOREIGN PATENT DOCUMENTS

EP     01172637     1/2003

(Continued)

OTHER PUBLICATIONS

DC Adler, et al., "Phase-Sensitive Optical Coherence Tomography at up to 370,000 Lines Per Second Using Buffered Fourier Domain Mode-Locked Lasers", Optics Letters, vol. 32, No. 6, pp. 626-628, (2007). Abstract Only.

(Continued)

*Primary Examiner* — Gregory J Toatley
*Assistant Examiner* — Scott Richey
(74) *Attorney, Agent, or Firm* — Thomas Meyers; Robert Tosti; Brown Rudnick LLP

(57) ABSTRACT

A method and a system for Uniform Frequency Sample Clocking to directly sample the OCT signal with a temporally-non-linear sampling clock derived from a k-space wavemeter on the external sample clock input port of a digitizer. The Uniform Frequency Sample Clocking comprises at least one Pathway, which includes characterizing the swept light source, creating a digital representation of the waveform based from the characterization data, and generating a clock signal using a waveform generator to output the clock signal to a digitizer external clock.

19 Claims, 14 Drawing Sheets

U.S. PATENT DOCUMENTS

| | | | | |
|---|---|---|---|---|
| 7,027,743 | B1 | 4/2006 | Tucker et al. | 398/204 |
| 7,359,062 | B2* | 4/2008 | Chen et al. | 356/479 |
| 7,391,520 | B2 | 6/2008 | Zhou et al. | 356/479 |
| 7,414,779 | B2* | 8/2008 | Huber et al. | 359/333 |
| 7,463,362 | B2* | 12/2008 | Lasker et al. | 356/497 |
| 7,633,627 | B2* | 12/2009 | Choma et al. | 356/479 |
| 7,728,986 | B2* | 6/2010 | Lasker et al. | 356/497 |
| 7,936,462 | B2* | 5/2011 | Jiang et al. | 356/497 |
| 2003/0220749 | A1* | 11/2003 | Chen et al. | 702/31 |
| 2005/0078317 | A1 | 4/2005 | Law et al. | 356/484 |
| 2005/0171438 | A1* | 8/2005 | Chen et al. | 600/476 |
| 2006/0055936 | A1 | 3/2006 | Yun et al. | 356/479 |
| 2006/0187537 | A1 | 8/2006 | Huber et al. | 359/337.22 |
| 2006/0244973 | A1 | 11/2006 | Yun et al. | 356/511 |
| 2007/0015969 | A1 | 1/2007 | Feldman et al. | 600/160 |
| 2007/0038121 | A1* | 2/2007 | Feldman et al. | 600/476 |
| 2007/0161893 | A1 | 7/2007 | Milner et al. | 600/425 |
| 2007/0260138 | A1* | 11/2007 | Feldman et al. | 600/409 |
| 2008/0095714 | A1* | 4/2008 | Castella et al. | 424/9.3 |
| 2008/0097194 | A1* | 4/2008 | Milner | 600/425 |
| 2008/0154128 | A1* | 6/2008 | Milner | 600/427 |
| 2008/0291463 | A1* | 11/2008 | Milner et al. | 356/491 |
| 2009/0174886 | A1* | 7/2009 | Inoue | 356/479 |
| 2009/0174931 | A1* | 7/2009 | Huber et al. | 359/340 |
| 2009/0284749 | A1* | 11/2009 | Johnson et al. | 356/497 |
| 2009/0290167 | A1* | 11/2009 | Flanders et al. | 356/497 |
| 2010/0128348 | A1* | 5/2010 | Taverner | 359/572 |
| 2010/0220334 | A1* | 9/2010 | Condit et al. | 356/497 |

FOREIGN PATENT DOCUMENTS

| | | |
|---|---|---|
| JP | 2004-004080 | 1/2004 |
| WO | WO 2004-096049 | 11/2004 |
| WO | WO 2006-068875 | 6/2006 |

OTHER PUBLICATIONS

Alazartech, "Specifications for ATS660 125 MS/s 16-bit PCI Digitizer", Version 1.1A, www.alazartech.com.

MA Choma, et al., "Sensitivity Advantage of Swept Source and Fourier Domain Optical Coherence Tomography", Optics Express, vol. 11, No. 18, pp. 2183-2189, (2003).

Gage Applied Technologies, "Specifications for CompuGen 4300/4302 High-Speed Arbitrary Waveform Generator Card", (May 29, 2006), www.gage-applied.com.

Gage Applied Technologies, "Specifications for CompuScope 1610 Ultra-Fast Waveform Digitizer Card for PCI Bus", (Mar. 31, 2006), www.gage-applied.com.

Eigenwillig et al., "K-Space Linear Fourier Domain Mode Locked Laser and Applications for Optical Coherence Tomography", Optics Express, vol. 16, No. 12, pp. 8916-8937, (2008).

Herget et al., "Infrared Spectrum of Hydrogen Fluoride: Line Positions and Line Shapes. Part II. Treatment of Data and Results", Journal of the Optical Society of America, vol. 52, pp. 1113-1117, (1962).

Huber et al., "Amplified, Frequency Swept Lasers for Frequency Domain Reflectometry and OCT Imaging: Design and Scaling Principles", Optics Express, vol. 13, No. 9, pp. 3513-3528, (2005).

Huber et al., "Fourier Domain Mode Locking (FDML): A New Laser Operating Regime and Applications for Optical Coherence Tomography", Optics Express, vol. 14, No. 8, pp. 3225-3237, (2006).

SMRM Nezam, "High-Speed Polygon-Scanner-Based Wavelength-Swept Laser Source in the Telescope-Less Configurations with Application in Optical Coherence Tomography", Optics Letters, vol. 33, No. 15, pp. 1741-1743, (2008). Abstract Only.

Oldenburg et al., "Fast-Fourier-Domain Delay Line for In Vivo Optical Coherence Tomography with a Polygonal Scanner", Applied Optics, vol. 42, No. 22, pp. 4606-4611, (2003).

Sarunic et al., "Instantaneous Complex Conjugate Resolved Spectral Domain and Swept-Source OCT Using 3×3 Fiber Couplers", Optics Express, vol. 13, No. 3, pp. 957-967, (2005).

Vakoc et al., "Phase-Resolved Optical Frequency Domain Imaging", Optics Express, vol. 13, No. 14, pp. 5483-5493, (2005).

Wavelength References, "Specifications for OEM Calibrators: Hydrogen Fluoride Gas Cell HF", www.wavelengthreferences.com.

Written Opinion for International (PCT) Patent Application No. PCT/US2008/070010, mailed Oct. 8, 2008.

* cited by examiner

APPARATUS AND METHODS FOR UNIFORM FREQUENCY SAMPLE CLOCKING

CROSS-RELATED APPLICATIONS

The present application claims priority to U.S. Provisional Application Ser. No. 60/949,467, filed Jul. 12, 2007, incorporated by reference herein.

BACKGROUND

The invention is generally related to laser systems, and more particularly related to Optical Coherence Tomography systems and methods.

Optical Coherence Tomography ("OCT") generates cross sectional imaging of tissues with micro-scale resolution by measuring the echo time delay of backscattered or backreflected light. Fourier Domain OCT ("FD-OCT") can obtain a high sensitivity and imaging speed by acquiring the optical spectrum of light backscattered from a sample interfered with light from a single stationary reference reflector using an interferometer. Swept-Source OCT ("SS-OCT"), time-encodes the wavenumber (or optical frequency) by rapidly tuning a narrowband light source over a broad optical bandwidth.

The high speed tunable laser sources for SS-OCT exhibit a nonlinear or non-uniform wavenumber vs. time [k(t)] characteristic. As such, SS-OCT interferograms sampled uniformly in time [S(t), e.g., using an internal digitizer clock] must be remapped to S(k) before Fourier-transforming into the pathlength (z) domain used to generate the OCT image. This software remapping operation is undesirable due to decreased phase sensitivity (i.e., amplitude and phase errors introduced in the remapping procedure), image artifacts, computational inefficiency, and the bandwidth needed to record a remapping array [k(t)] for each OCT interferogram [S(t)].

Additionally, when operating at fast frequency sweep speeds, the laser frequency varies nonlinearly rather than linearly with time in SS-OCT. Therefore, an accurate and reliable recalibration of the interference output to equidistant spacing in wavenumber (k) or optical frequency (v) is necessary. Also, nonlinearity may arise from the specifics of the tunable element(s) in the source, which might be the type of tunable filter (e.g., mechanical rotating mirror in combination with a grating, fabry perot, ect.), the operation of the tunable filter or time varying operation (drift) of the tunable filter. Analog-Digital ("A/D") converter cards that operate at lower frequencies, i.e. low-speed digitizers, are not practical for the high-speed OCT systems. Moreover, most high speed A/D converter cards have a timing jitter of the generated clocking signal, which can degrade images recorded using SS-OCT. Most high-speed digitizers are very selective about the timing parameters of their external clock, i.e. duty cycle, pulse shape, amplitude, jitter, etc. Thus, the external clocking is difficult without some way of processing, whether analog or digital.

High-speed digitizers operating with an internal sample clock and swept-source lasers used for OCT must have a calibration performed between the non-linear sweep of the laser and the constant sampling frequency of the digitizer. This may be accomplished using software post-processing interpolation method of a linearly-sampled (in time) calibration k-space wavemeter signal or a non-uniform Fourier transform. Despite these approaches, obtaining a uniformly-sampled signal in wavenumber (k) or optical frequency (v) improves OCT image quality and display rate. Unfortunately, today's high-speed digitizers have stringent requirements on the continuity of the amplitude and frequency of the external sample clock input, and disruptions in the wavemeter signal for example at times when the laser is between successive sweeps can disable the digitizer's internal sampling circuitry. The embodiments described herein solve these problems, as well as others.

SUMMARY OF THE INVENTION

The method and a system for uniform frequency sample clocking directly samples the OCT signal with a temporally-non-linear sampling clock derived from a k-space wavemeter on the external sample clock input port of a digitizer.

The foregoing and other features and advantages are defined by the appended claims. The following detailed description of exemplary embodiments, read in conjunction with the accompanying drawings is merely illustrative rather than limiting, the scope being defined by the appended claims and equivalents thereof.

BRIEF DESCRIPTION OF THE DRAWINGS

The foregoing description of the figures is provided for a more complete understanding of the drawings. It should be understood, however, that the embodiments are not limited to the precise arrangements and configurations shown.

DETAILED DESCRIPTION OF THE INVENTION

The methods, apparatuses, and systems can be understood more readily by reference to the following detailed description of the methods, apparatuses, and systems, and the accompanying figures.

Figure 1:
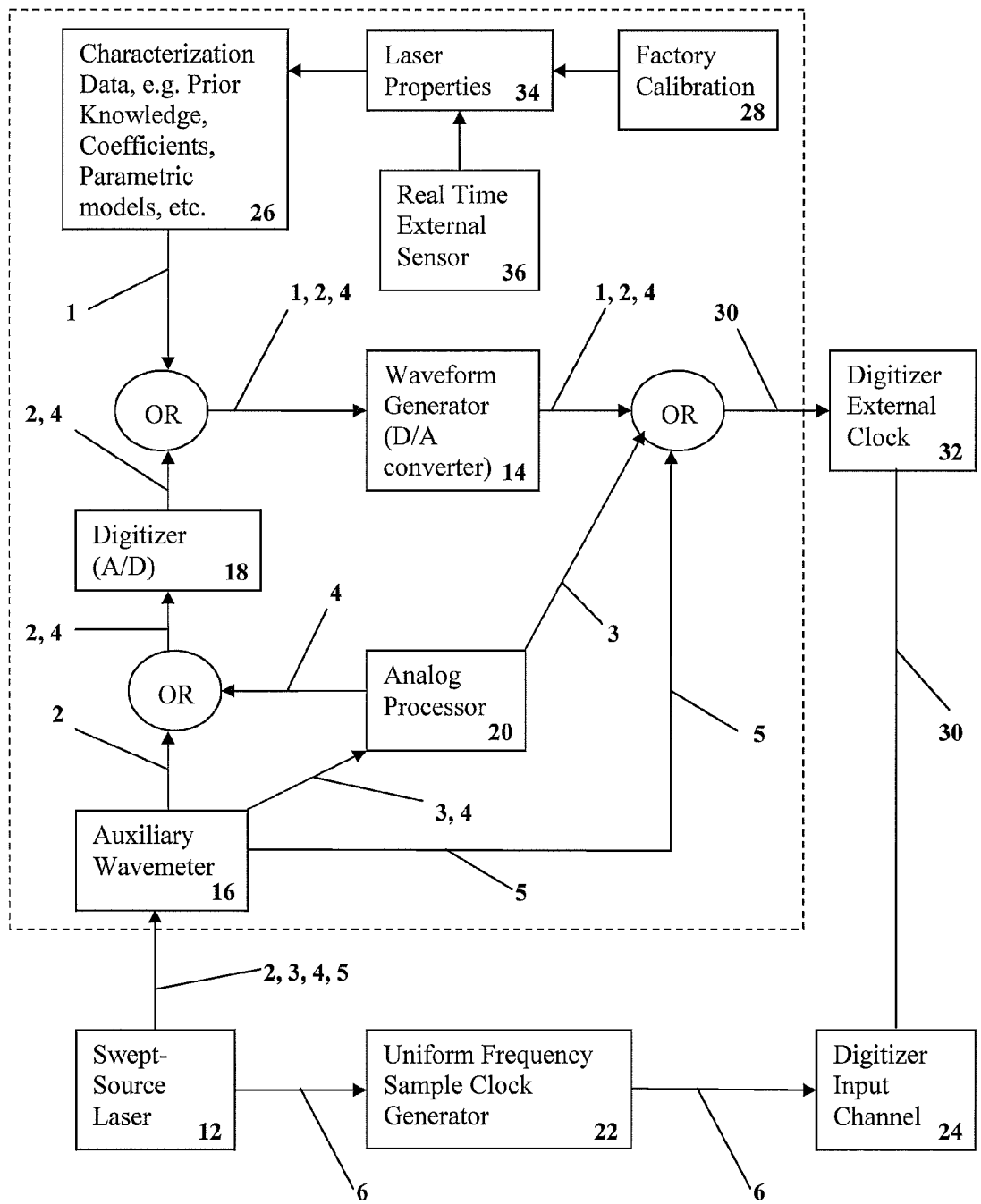
FIG. 1 is a schematic of the Uniform Frequency Sample Clock Pathways for the external clocking of a swept laser source.

Generally speaking, a Uniform Frequency Sample Clocking 10 systems and methods for a swept laser source 12 are generally shown in FIG. 1. The Uniform Frequency Sample Clocking 10 comprises at least one Pathway, where some embodiments of the Pathways are generally shown as line arrows in FIG. 1. The line arrows represent electronic or optical coupling elements, such as wires, fibers, and the like. In one embodiment, Uniform Frequency Sample Clocking 10 includes Pathway 1 comprising characterizing 26 the swept laser source 12, creating a digital representation of the waveform based from the characterization data 26, and generating a clock signal 30 using a waveform generator 14 (i.e. a Digital-Analog ("D/A") converter) to output the clock signal 30 to a digitizer external clock 32. The Uniform Frequency Sample Clocking 10 may include Pathway 2 comprising coupling the swept laser source 12 to an auxiliary wavemeter 16, digitally processing the auxiliary wavemeter 16 output with an Analog-Digital ("A/D") digitizer 18, and processing the digitizer's 18 output on the D/A converter 14 to generate the clock signal 30 outputted to the digitizer external clock 32. The Uniform Frequency Sample Clocking 10 may include Pathway 3 comprising coupling the swept laser source 12 to the auxiliary wavemeter 16 and processing auxiliary wavemeter 16 output using an analog processor 20 to generate the clock signal 30. The Uniform Frequency Sample Clocking 10 may include Pathway 4 comprises coupling the swept laser source 12 to the auxiliary wavemeter 16, processing the auxiliary wavemeter 16 output with the analog processor 20, digitizing the analog processor's 20 output with the digitizer 18, digitally processing the auxiliary wavemeter 16 output with the D/A converter 19 to generate the clock signal 30. The Uniform Frequency Sample Clocking 10 may include Pathway 5 comprising coupling the swept laser source 12 to the auxiliary wavemeter 16 to directly generate a uniform-frequency sample clock signal with no pre-processing. The Uniform Frequency Sample Clocking 10 may include Pathway 6 coupling the swept laser source 12 to a Uniform Frequency Sample Clock Generator 22 outputting to a digitizer 24 to generate the clock signal 30. The Uniform Frequency Sample Clocking 10 systems and Pathways provide for external clocking of the swept laser source 12 and can provide a different clocking signal through independent Pathways, in combination and in any particular order, to generate the clock signal, process the clock signal, and transmit the clock signal to the digitizer for uniform sampling of detected light in the wavenumber domain. For each acquisition channel, one clock signal may be active at a given time, which may be switched between different clock signals in any particular combination or order. Alternatively, the Uniform Frequency Sample Clocking 10 Pathways may be combined with each other, in any sequence of combinations. More particularly, the Uniform Frequency Sample Clock Pathways 10 provide external clocking of detected light first emitted from the swept laser source for OCT systems. The term "Uniform Frequency Sample Clocking" and "linear sampling in the wavenumber domain" are equivalent terms, as used in the specification. The term "external clock signal" is specific to the type of signal applied to the external clock signal input or the clock signal input of the digitizer external clock 32. The term "clock signal" is the signal as applied to the AD converter card.

The swept source 12 includes emitted light with a mean frequency of the output spectrum that varies over time. The term "swept source" is synonymous with a "tunable source", i.e. tuning a light source over a period of time at a certain frequency. The mean optical frequency of light emitted from the swept source may change continuously over time at a tuning speed that is greater than 100 terahertz per millisecond and repeatedly with a repetition period. And the range of sweep speeds for the tunable source is specifying a range of sweep speeds (e.g., 10,000-10,000,000 Sweeps/sec). The swept source 12 may be any tunable source that rapidly tunes a narrowband light emission through a broad optical bandwidth. The tuning range of the swept source may have a tuning range with a center wavelength between approximately 500 nanometers and 2000 nm, a tuning width of approximately greater than 1% of the center wavelength, and an instantaneous line width of less than approximately 10% of the tuning range. Alternatively, more than one optical source may be combined to produce the swept source, or a continuously swept multi-wavelength emitting several optical frequencies or wavelengths simultaneously. While tunable light sources and swept-source lasers are included as the swept source, Fourier Domain Mode Locking ("FDML") lasers may be included as the swept source as well as Superluminescent Diodes (SLDs). In FDML, the spectrum, rather than the amplitude of the field, is modulated. A dynamic spectral window function (wavelength window which changes in time), rather than a temporal one (time window with no wavelength dependence), is applied. As a result, the laser generates a sequence of narrowband optical frequency sweeps at the cavity repetition rate or a harmonic thereof. Multiple tunable wavelength sources may included with, where each tunable wavelength source has a receiver, so each tunable wavelength source is coupled with a detector. The composite of all the tunable wavelength laser sources and detectors can act as very large bandwidth light source. This frequency-swept output can also be thought of as a sequence of highly chirped, long pulses, with a fixed phase relationship between successive frequency sweeps.

Figure 2:
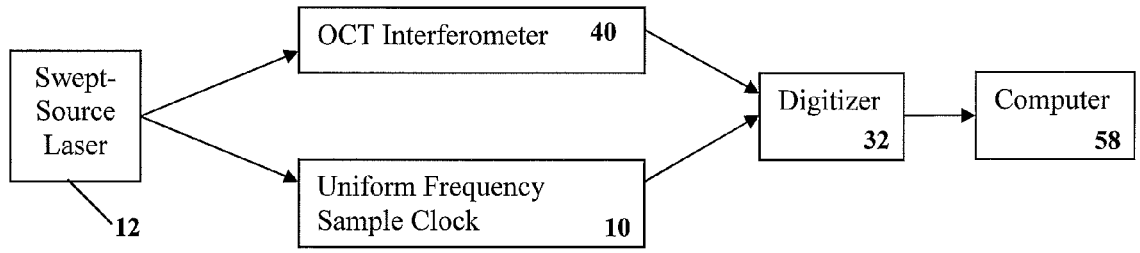
FIG. 2 is a schematic of one embodiment of the Uniform Frequency Sample Clock coupled with an OCT Interferometer.

In one embodiment, the swept laser source 12 provides the swept optical output to an OCT interferometer 40 and the Uniform Frequency Sample Clock 10, as shown in FIG. 2. Light emitted from the swept laser source 12 is split between the OCT interferometer 40 and the uniform frequency sample clock 10. The swept laser source 12 may be split in any desired ratio, including, but not limited to 95/5, 90/10, 85/15, 80/20, etc. to the OCT interferometer 40 and the Uniform Frequency Sample Clock 10, respectively. The Uniform Frequency Sample Clock 10 and the OCT interferometer 40 are then coupled to the digitizer 32 and then to a computer for processing and imaging.

Figure 15:
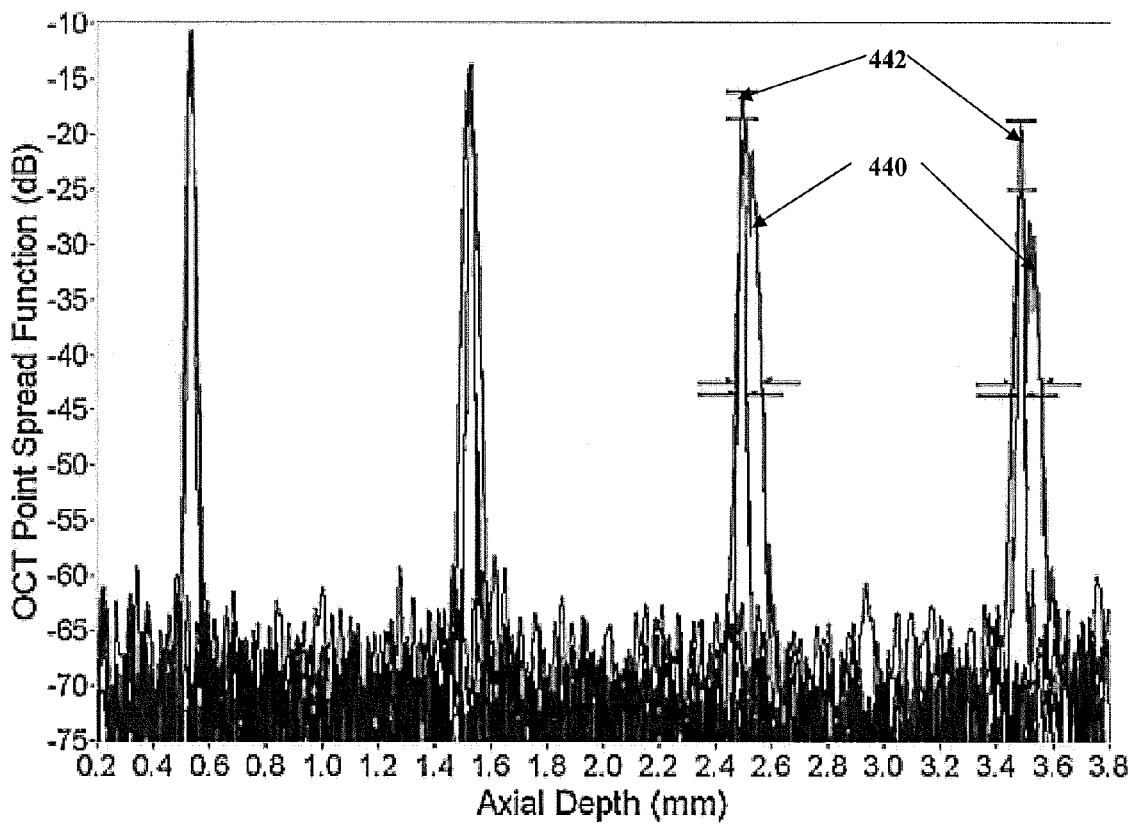
FIG. 15 is an OCT point spread functions vs. depth for an internally clocked/remapped scheme (440) and the externally clocked scheme 442

The OCT interferometer 40 splits the light emitted from the swept source to a reference surface and a sample arm, which recombines at the output of the interferometer. The OCT interferometer may take any of the variety of configurations known in the art, including, but not limited to, a Michelson interferometer, a Mach-Zehnder Interferometer, and/or a common path interferometer, etc. The Uniform Frequency Sampling clock generator 22 receives light from the swept source or the previously characterized swept source data and outputs to the digitizer to provide linear sampling in the wavenumber (k) or optical frequency (v) domain, allowing direct Fourier transformation into the pathlength (z) domain for real time OCT imaging. The real-time OCT imaging comprises (1) Uniform Frequency Sampling; and (2) direct Fourier transformation of fringe data for real-time OCT imaging. Direct Fourier transformation requires a digital processing element that does the Fourier transform of the Uniform Frequency Sampled OCT fringe data or the "OCT signal data". Uniform Frequency Sampled OCT fringe data or the "OCT signal data" are used synonymously throughout. Generally speaking, the Uniform Frequency Sample clock 10 provides for linear sampling in the wavenumber domain, digitizing the OCT fringe data in the wavenumber domain for real-time OCT imaging, and combinations thereof. FIG. 15 compares axial point spread functions and OCT images generated with uniform time sampling vs. the uniform frequency sample clocking approach 10 using the Pathways discussed below.

Pathway 1: Characterizing the Swept Laser Source

In one embodiment, the Uniform Frequency Sample Clock 10 includes Pathway 1 comprising a step of characterizing light emitted by the swept laser source 12, creating a digital representation of the waveform based on the characterization data 26, and repeatedly outputting the characterization data 26 for each subsequent optical trigger that occurs as the laser is sweeping, as shown as Pathway 1 in FIG. 1. Data for characterizing light emitted from the swept laser source ("characterization data") is generated using a high-speed D/A converter, i.e. the waveform generator 14, which is then coupled to the digitizer's 32 external clock input port. The D/A converter 14 outputs the generated Uniform Frequency Sample Clock signal for each laser sweep, triggered by an electrical synchronization pulse or an optical trigger 54 derived from the swept-source laser output. There are several ways to generate the optical trigger 54. In one embodiment, the optical trigger 54 is generated from an optical trigger generator 60, discussed below. In another embodiment, the optical trigger 54 is derived from an optical tuning element in the swept laser source, as the signal may be generated actively or passively. When light is emitted from the swept laser source and interacts with an optical tuning element at the output of the swept laser source, the optical trigger signal is provided. The optical tuning element may be static and does not necessarily need to be actively tuned to function in the role providing the optical trigger signal. Another embodiment to generate the optical trigger 54 is to sample the light with an optical frequency selective element, i.e. a grating spectrometer, interference filter, Fabry-Perot filter, and the like, or combination there-of, and a photo-detector coupled to an A/D converter to provide the optical trigger. So there may be two different optical tuning elements, one within the laser source that functions to tune the laser and one that can be placed at the output of the tuning laser source, which can be used to provide a trigger signal. Combinations of these optical tuning element embodiments can be employed to generate an optimum optical trigger 54.

Figure 3:
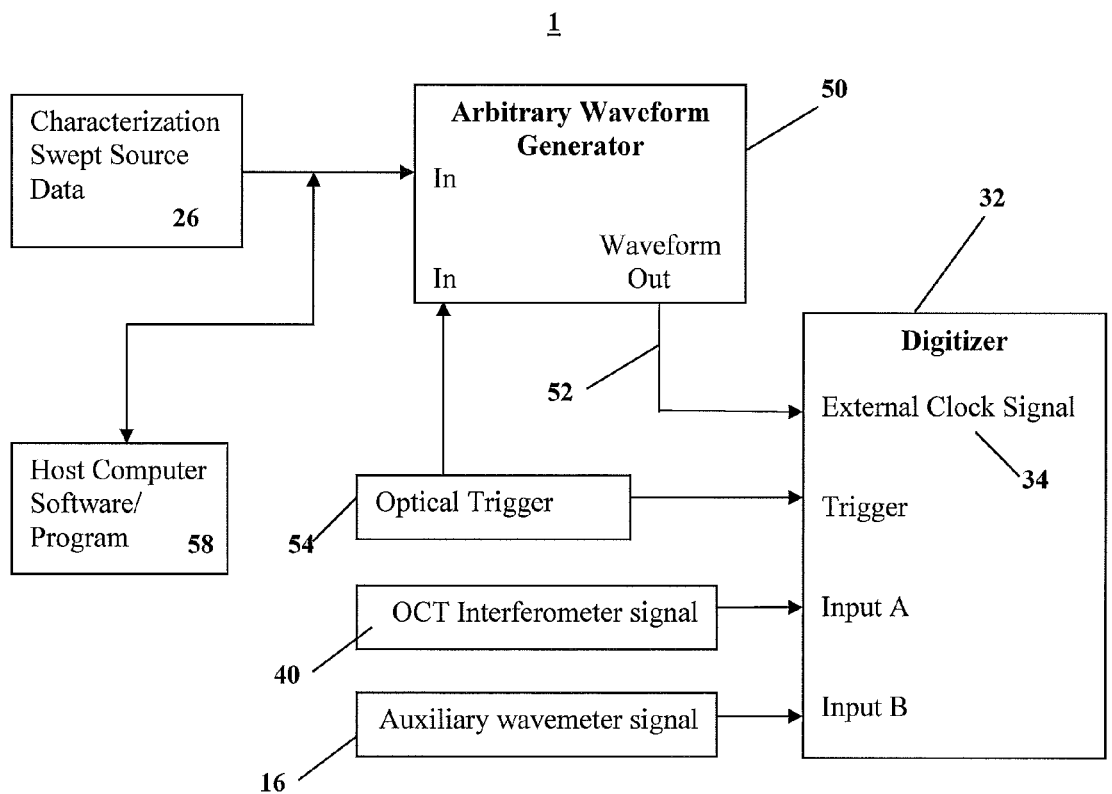
FIG. 3 is a schematic of one embodiment of Pathway 1.

In one embodiment, the D/A converter 14 may comprise an arbitrary waveform generator 50, as shown in FIG. 3. The arbitrary waveform generator 50 (CompuGen, Lockport, Ill.) provides aperiodic or periodic analog waveforms 52 as their output and generates a pre-programmed waveform every time a trigger event occurs. The pre-programmed waveform is stored in the on-board memory of the arbitrary waveform generator. Arbitrary waveforms 52 are generated by creating a digital representation of the waveform based on the characterization data 26 of light emitted from the swept laser source in the memory of the arbitrary waveform generator. The digital representation pattern is converted into an analog signal using a high-speed Digital-to-Analog converter and conditioning amplifiers (buffers and attenuators) within the arbitrary waveform generator 50. The external clock signal 34 is derived from the characterization data of the swept source during a start-up calibration step, and then repeatedly outputted by the arbitrary waveform generator for each subsequent optical trigger 54 signal that occurs as the laser is sweeping. Alternatively, the external clock signal 34 from characterization data 26 can also be completed periodically according to some schedule programmed by a computer software 58, or may be performed in response to some event such as a parameter (or combination of parameters) of the source changing (e.g., temperature). The uniform frequency sample clock by the characterization of the swept laser source data 26 allows acquisition (analog to digital conversion) of OCT interferometer 40 data directly in wavenumber (k) space.

As shown in FIG. 1, characterizing the swept laser source data 26 may include a factory calibration 28 of the swept laser source; obtaining laser properties 34 of the laser source; or obtaining a parametric model of the swept laser source. The factory calibration 28 of the swept laser source may be obtained from the manufacturer of the swept laser source. Obtaining laser properties 34 of the laser source comprises a real time external sensor to obtain optical and environmental data about the swept laser source, such as temperature, position of optical elements, gradient, etc. The characterization data 26 may include prior knowledge about the swept laser source in the form of coefficients, a look-up table, or the parametric model to generate the clock signal. A lookup table (LUT) is a data structure, usually an array or associative array, used to replace a runtime computation with a simpler array indexing operation. The speed gain can be significant, since retrieving a value from memory is often faster than undergoing an expensive computation or by giving an output value for each of a range of index values. The parametric model of the laser source can be relied on to generate the swept laser source characterization data. The swept laser source characterization data may be obtained from the parametric model and a real-time measurement of one or more properties of the swept laser source. A parametric model is a set of related mathematical equations in which alternative scenarios are defined by changing the assumed values of a set of fixed coefficients (i.e. parameters). The parametric model is specified by a functional relationship between model parameters, where some of the parameters can be measured in real time and other parameters are fixed or factory values. By imputing the model parameters into the parametric model, the swept laser source characterization data may be generated. The parametric model can be provided with a software program in a host PC 58 to create a digital and then analog representation, as shown in FIG. 3. The analog representation will require a D/A converter or waveform generator, as described previously. All such characterization data 26 is outputted to the arbitrary waveform generator to give a Uniform Frequency Sample Clock signal for the digitizer.

Pathway 2: Auxiliary wavemeter coupled with a A/D and D/A converter

Figure 4A:
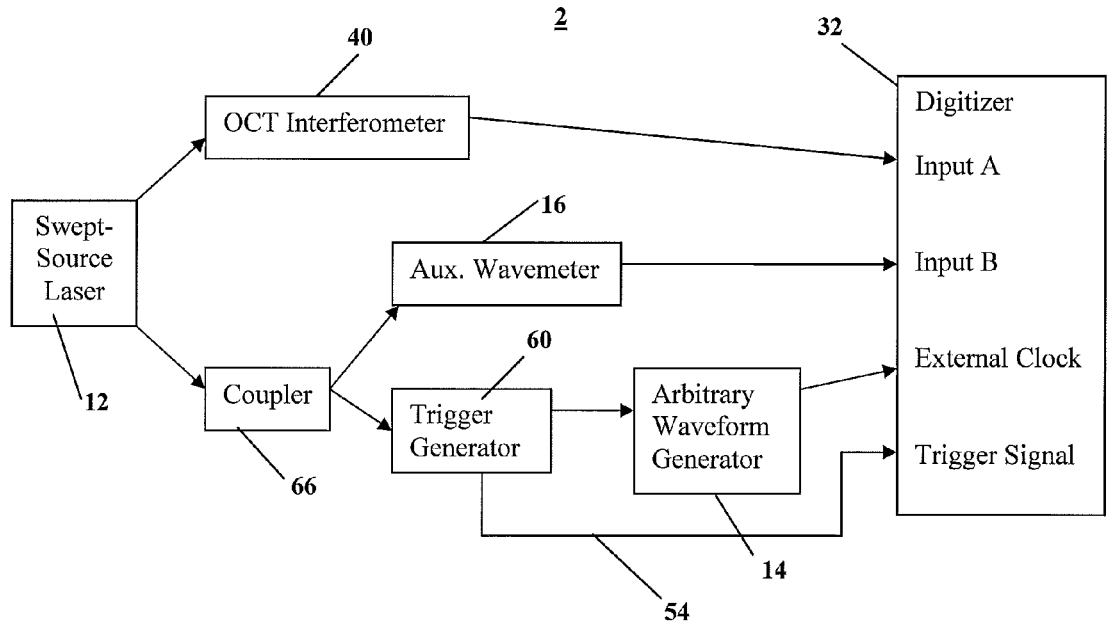
FIG. 4A is a schematic of one embodiment of Pathway 2.

In one embodiment, the Uniform Frequency Sample Clock 10 includes Pathway 2 comprising coupling the swept source 12 to the auxiliary wavemeter 16 and the A/D converter or digitizer 18, as shown in FIG. 4A. The A/D converter 18 is an electronic internal circuit that converts continuous analog signals to discrete digital numbers. The D/A converter, otherwise known as the arbitrary waveform generator 14, is then used to output a digitally-processed Uniform Frequency Sample Clock signal 30 to the external clock signal 34 input of the digitizer 32. The Uniform Frequency Sample Clock signal 30 is repeatedly outputted for each subsequent optical trigger 54 that occurs as the laser is sweeping the optical trigger is generated. The optical trigger 54 may be generated by any of the previously discussed methods.

Figure 4B:
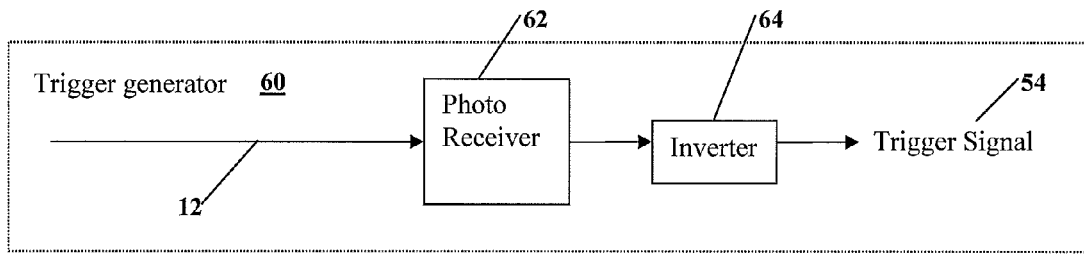
FIG. 4B is a schematic of the trigger generator.

For one embodiment of Pathway 2, a portion of the light emitted from the swept source 12 is coupled to the auxiliary wavemeter 16 and the optical trigger generator 60 via a 50/50 coupler 66 or an arbitrary splitting coupler, which splits the light into the auxiliary wavemeter 16 and the optical trigger generator 60. The auxiliary wavemeter 16 may be any type of wavemeter, including, but not limited to, a Mach-Zehnder, Michelson, or a Fabry-Perot interferometer. Fabry-Perot interferometers are preferred if the OCT interferometer 40 is phase-sensitive. If the OCT interferometer 40 system is not phase-sensitive, then Mach-Zehnder, Michelson interferometers, or etalons may be used as the auxiliary wavemeter 16. As shown in FIG. 4B, in one embodiment of Pathway 2, the optical trigger generator 60 includes a photoreceiver 62 and an inverter 64 to generate an electronic trigger signal 54, based on Transistor-Transistor Logic ("TTL"). TTL digital circuits are built from bipolar junction transistors, and resistors with both the logic gating function (e.g., AND, Inversion, etc.) and the amplifying function are performed by transistors. The optical trigger generator 60 generates the electronic trigger signal 54 according to when the swept source laser 12 light is being emitted. The trigger signal 54 is used to synchronize the digitizer 32 and arbitrary waveform generator 14 electronics when the laser has begun a sweep of its light emission. In another embodiment of Pathway 2, the optical trigger generator 60 may be derived from the tuning element in the swept laser source, either the transducer driving the tuning element or some transducer reading the tuning element (e.g., encoder or interferometric signal), which might be light based. Alternatively, the optical trigger generator 60 may be derived by sampling the light emitted from the swept laser source, where the sampling element can be one or more combinations of optical frequency selective elements, as discussed previously. Combinations of these approaches can be employed for the optical trigger generator 60.

Figure 4C:
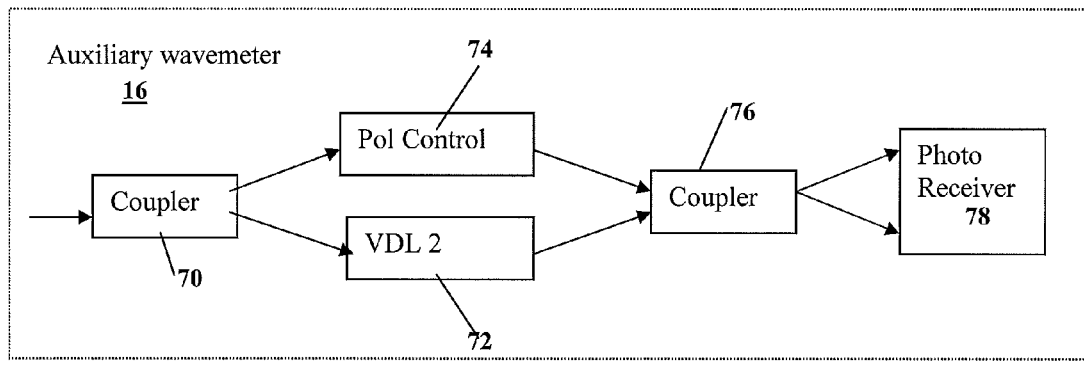
FIG. 4C is a schematic of the auxiliary wavemeter.

As shown in FIG. 4C, in one embodiment, the auxiliary wavemeter 16 is a Mach-Zehnder interferometer, where the input from the coupler 66 extends into a 50/50 coupler 70 to separate the Mach-Zehnder into two output paths. A first output path from the coupler 66 extends into a Variable Delay Line VDL 72, a second output path from the coupler 66 extends to a Polarization Controller 74. The variable delay line 72 system consists of an input fiber, a retro-reflecting mirror on a translation stage, and an output fiber. A manual dial or electrical motor controls the variable length, or delay, inserted into the optical path, as selected according to various factors of the swept laser source being used. The pathlength delay determines the clock frequency. Both the polarization controller 74 and the VDL 72 extend to a 50/50 coupler 76, which recombines the separate paths of the Mach-Zehnder interferometer to dual-balanced photoreceiver 78.

Figure 5:
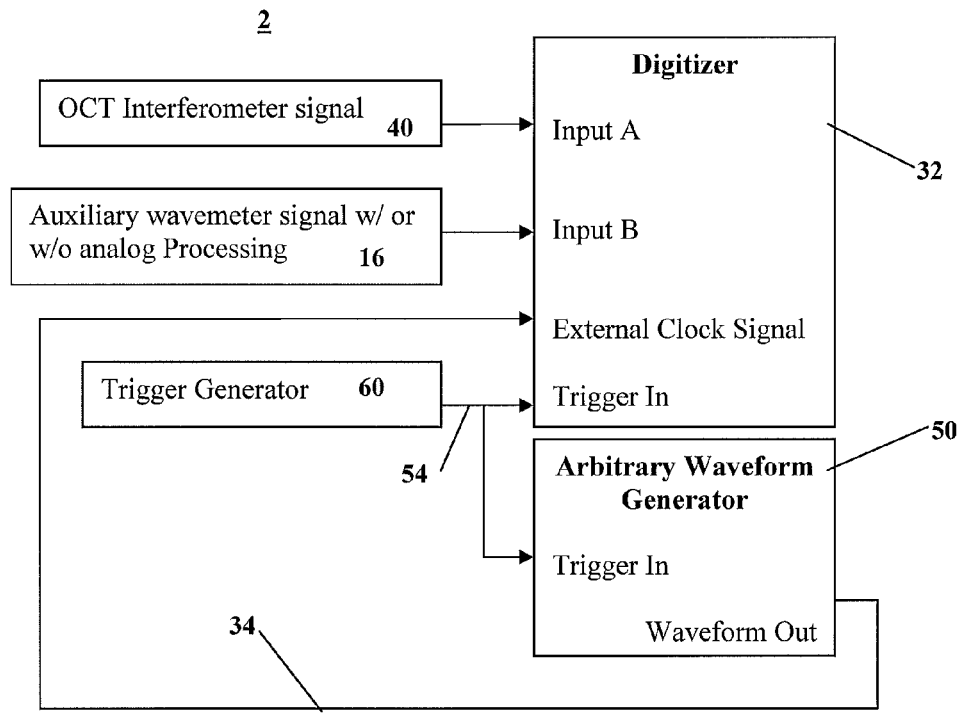
FIG. 5 is a schematic of the digitizer with the arbitrary waveform generator.

In one embodiment of Pathway 2, the Uniform Frequency Sample Clock 10 generates an external sample clock signal 34 linked to the high-speed digitizer card 32, as shown in FIG. 5. The high-speed digitizer card 32 is coupled to the output of the OCT interferometer 40, the output of the auxiliary wavemeter 16, the trigger signal 54 from the trigger generator 60, and the arbitrary waveform generator 50. The high-speed PCI digitizer card 32 can be a dual-channel high resolution 16 bit, 125 MS/s waveform for the PCI bus. The external sample clock signal 34 is derived from an auxiliary optical wavemeter photoreceiver 78 during a start-up calibration step, and then repeatedly outputted by the arbitrary waveform generator 50 for each subsequent optical trigger signal 54 that occurs as the laser is sweeping. The external clocking system of Pathway 2 allows for the wavemeter-generated clock signal to be filtered and processed in software before being outputted by the arbitrary waveform generator 14. Thus, the external clock derived from the auxiliary wavemeter 16 is regenerated by the arbitrary waveform generator 50 (Gage CompuGen) to allow acquisition of data directly in wavenumber (k) space.

Figure 6A:
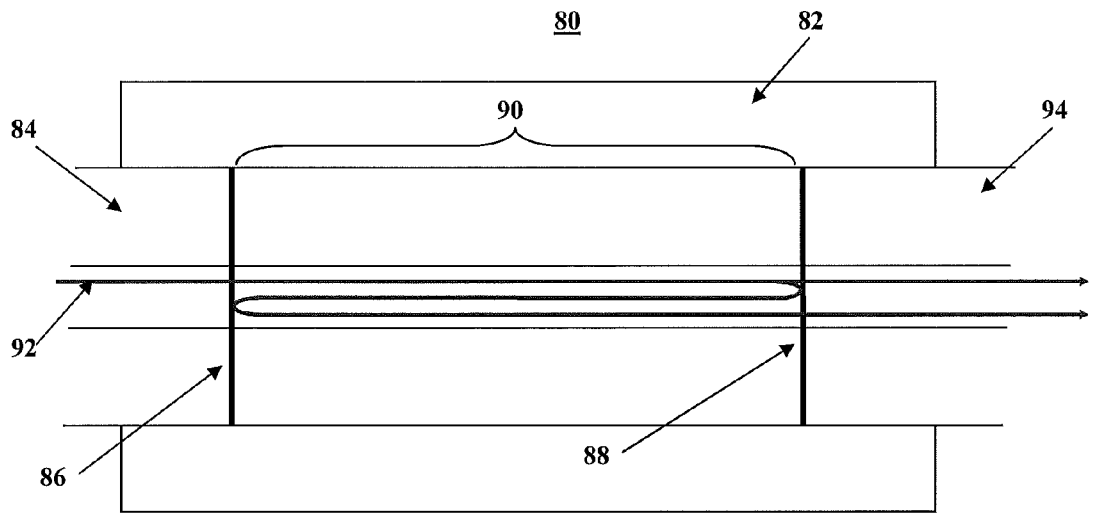
FIGS. 6A and 6B are cross-sectional view of schematics for alternative embodiments of the auxiliary wavemeter.
Figure 6B:
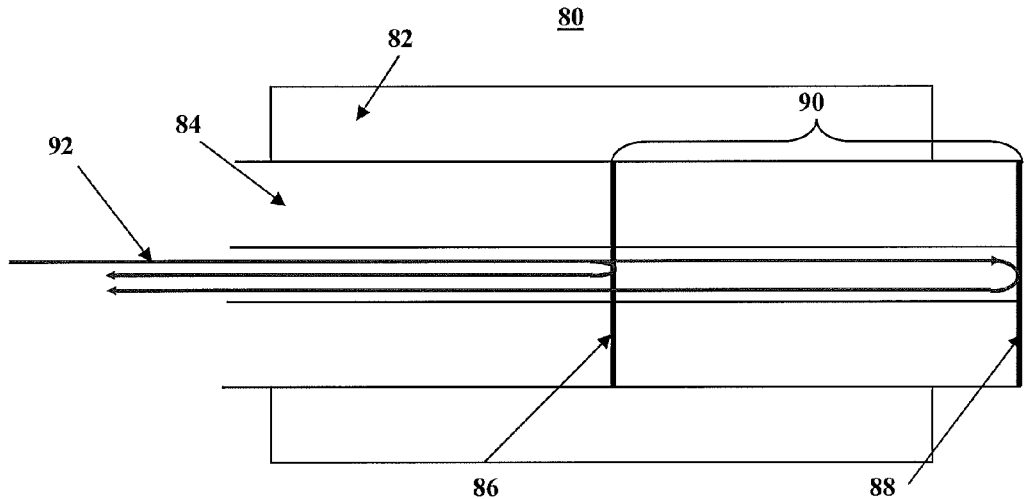

In another embodiment of Pathway 2, the auxiliary interferometer 16 is a Fabry-Perot interferometer, as shown in FIGS. 6A and 6B. FIG. 6A shows a transmission mode Fabry Perot interferometer 80 made from a ferrule 82 having an internal diameter the same OD as the optical fiber cladding connected from the coupler. The transmission mode ferrule 82 includes a single mode (SM) optical fiber 84 with a first interface 86 and a second interface 88, where each interface is coated with a metal or dielectric material to achieve a desired reflectively. The optimum reflectivity at each interface will be chosen to maximize interference fringe visibility (i.e., matched intensity reflected from each interface into detection path) as is known in the art of fiber Fabry-Perot interferometers. Reflectivity can be controlled by coating the intermediate fiber segment 90 of the SM fiber 84 with a carefully-deposited metal or dielectric surface on each end during assembly. For example, to calculate the optimum reflectivity (R1) of the first interface in transmission mode, the following quadratic equation is solved so that the two interfering beams have the same intensity (and max visibility): $R1=(1-R1)^2$, which is solved as: $R1=38.1\%$. Quadruple and higher-order reflections will produce harmonics, with much reduced intensity, in the fringe signal, which can processed electronically with a filter. Control of temperature of the fiber Fabry-Perot interferometer's thermal expansion/contraction to maintain a stable path-length difference provides a control for variable frequency wavemeter output.

The intermediate portion of the fiber segment 90 lies in between the first and second interface of the transmission mode ferrule. The birefringence in the intermediate fiber portion must be kept to a minimum so that both reflections will have the same polarization state. The optical path length is chosen based on desired interference fringe frequency, which can be 4 mm-6 mm for most OCT swept sources. The double-pass path length determines the clock frequency, as opposed to the single pass pathlength. The pathlength can be longer, for example in some implementations the optical path length is 10 mm, which can vary to different optical path lengths, from 5-20 mm. The pathlength delay in the Fabry-Perot determines the clock frequency as in other clocking interferometers.

The light 92 from swept laser source enters through input fiber 84 of the ferrule 82. Some light is partially reflected at the first interface 86 within the intermediate fiber segment 90 and then discarded; possibly needing an optical isolator to protect the source. The remaining light is transmitted through intermediate fiber segment 90 and partially reflected at second interface 88. The reflected portion is transmitted back to first interface, where the light is again partially reflected. Transmitted light is discarded as previously and reflected portion makes a second forward propagation through intermediate fiber segment 90 and is partially transmitted at second interface 88 into an output or collection fiber 94. This portion interferes with the portion transmitted into the output fiber from the second interface on the initial reflection. Thus the path length delay sets the sampling of the optical frequency signal. The path length delay between the two transmitted portions is twice the optical path length of the intermediate fiber segment. And the path length delay sets the sampling of the optical frequency signal. Detection of the interference fringes is accomplished after collection of the light with the output fiber, which is coupled to a photoreceiver and the high speed digitizer as the auxiliary wavemeter 16 signal, as previously indicated, to directly clock the swept source or resample the wavemeter 16 signal in a post-acquisition step.

In another embodiment of the auxiliary interferometer 16, as shown in FIG. 6B, the reflection mode Fabry Perot interferometer 80 includes the ferrule 82 having an internal diameter the same OD as the optical fiber cladding connected from the coupler. The reflection mode ferrule 82 is coupled to a polarization-insensitive circulator (not shown) and a single mode optical fiber 84 with a first interface 86 and a second interface 88, where each interface is coated with a metal or dielectric material to achieve appropriate reflectively, as indicated previously. The SM fiber 84 includes an end portion of the fiber segment 90 that lies in between the first and second interface 86 and 88. The optical path length is chosen based on desired interference fringe frequency, which can be about 2 to about 1000 mm for most OCT swept sources. Light 92 from swept laser source enters port 1 of a polarization-insensitive optical circulator and is send outward on port 2. The fiber comprising port 2 becomes the input fiber to the inline delay device. Light 92 is partially reflected at first interface 86 within optical fiber 84. Then, the transmitted portion forward-propagates to the second interface 88, which has a maximum reflectivity. Light reflected from the second interface 88 backward-propagates to the first interface 86, where the light is partially reflected again as a second partially reflected light. The transmitted portion from the second partially reflected light beam and the reflected portion from the original incident beam then interfere and are collected on port 3 on the circulator where they are then detected by a photoreceiver, which is coupled to the high speed digitizer as the auxiliary wavemeter signal, as previously indicated.

An etalon is not substantially different from a Fabry-Perot, as the two terms are used interchangeably in the art as Fabry-Perot etalon. The Fabry-Perot etalon can be a fiber version or a free-space version. In the etalon approach, incident light (free-space) is multiply-internally reflected in a highly-controlled and wavelength-specific manner such that internal interference allows transmission of wavelengths in a periodic fashion. Frequency of this periodic transmission function depends on the thickness of the etalon and the laser sweep speed ($cm^{-1}/s$ or Hz/s). Adverse environmental effects are reduced by having light propagated along a common path, and high finesse provided by careful control of the facet reflectivity is required.

Figure 7:
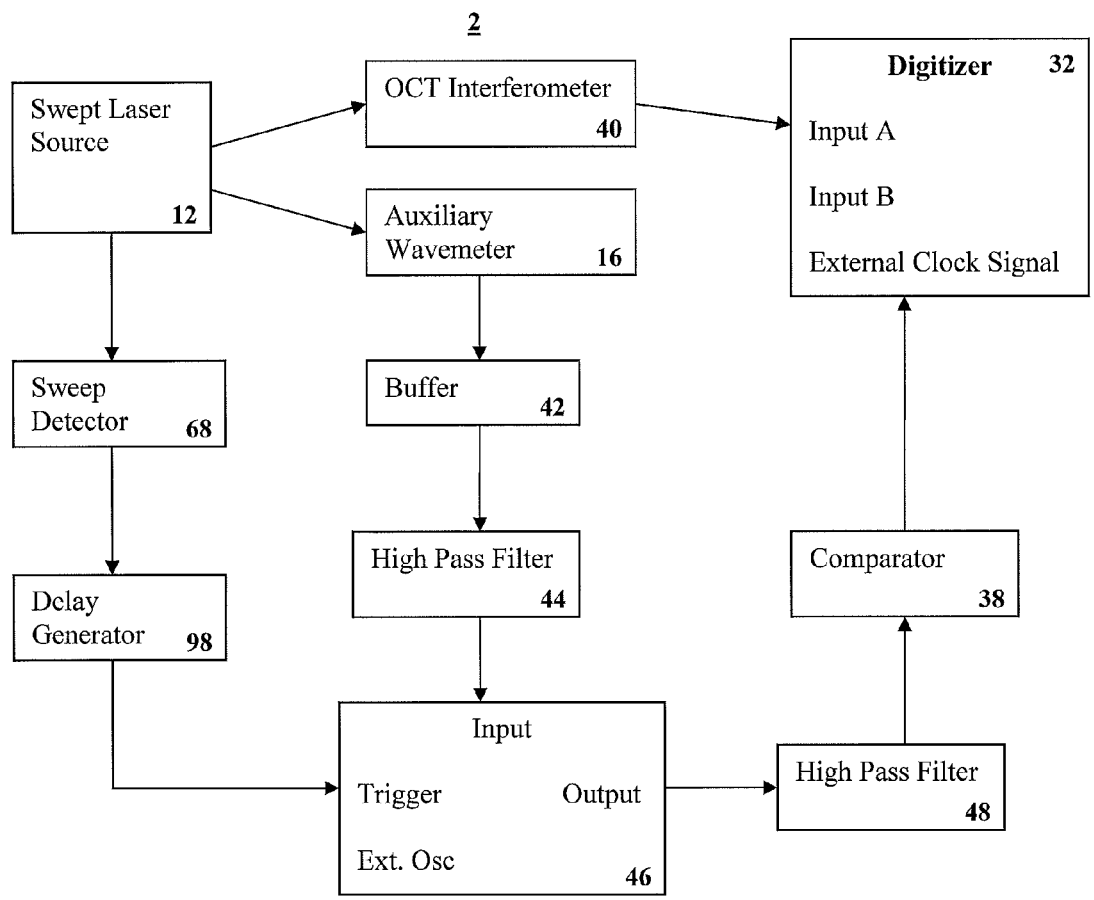
FIG. 7 is a schematic of one embodiment of Pathway 2.

In another embodiment, Pathway 2 comprises coupling the swept laser source 12 to the auxiliary wavemeter 16 and a sweep detector 68, as shown in FIG. 7. As the swept laser source 12 starts its sweep, the sweep detector 68 collects an intensity profile of the laser sweep, which is fed into a Delay Generator 98. The Delay Generator 98 has a comparator built in so that it can shape the intensity profile of the laser into a square wave. This square wave can be varied in length from 20-50 uS, depending on what is needed. This 20-50 uS wavelength is dependent on the laser can be easily modified to for different laser sweep speeds and duty cycles. This shaped square wave is then fed into a switching circuit 46.

The OCT Interferometer 40 operates normally; sending the OCT fringe signal data to the digitizer 32 that is clocked by the process that occurs with the auxiliary wavemeter 16. The auxiliary wavemeter 16 can be any of the previously described wavemeters, Mach-Zehnder, Michelson, Fabry-Perot, inline Fabry-Perot, and the like. The auxiliary wavemeter 16 creates an interference pattern that has a non-uniform frequency in time, based on the path length mismatch when the laser is operating. This auxiliary wavemeter 16 signal is converted to an electrical signal using a balanced photodetector, which is then passed into a circuit that includes a buffer 42 and a high pass filter 44. The signal is buffered for impedance matching purposes, and then the signal is directed into the high pass filter 44 to remove low frequency components than a cutoff frequency. The filtered signal is then directed into an electronic switch circuit 46. The electronic circuit switch establishes connections between links, on demand and as available, in order to establish an end-to-end circuit between devices. The connections are temporary, continuous, and exclusive in nature. When the laser power is less than the threshold level or the wavelength of the laser sweep is outside of a certain range (i.e. a false condition), the trigger signal from section is 0 volts, and 5V when the condition is true. The output of the switch circuit 46 is an external clock when a 0V signal into the trigger of the switch circuit 46. This external clock is not tied to the laser in any way and is always running. The output of the switch circuit 46 is the filtered signal from the auxiliary wavemeter 16 when the trigger voltage is 5V (when the condition is true). This satisfies the condition of some A/D cards to always have a clock on the input, even while the laser is not on.

Regardless of the output of the switch circuit 46, the signal is high pass filtered through the high pass filter 48. The signal from the high pass filter 48 is coupled into a high speed comparator 38. A comparator is a device which compares two voltages or currents and switches its output to indicate which is larger. The high speed comparator 38 converts the signal from the high pass filter into a square wave that has a voltage level compatible with the digitizer 32 external clock input parameters. The high pass filter 48 and comparator 38 help clean up the signal. The signal is then fed into the external clock on the digitizer 32 A/D card.

OCT Interferometer

Figure 8:
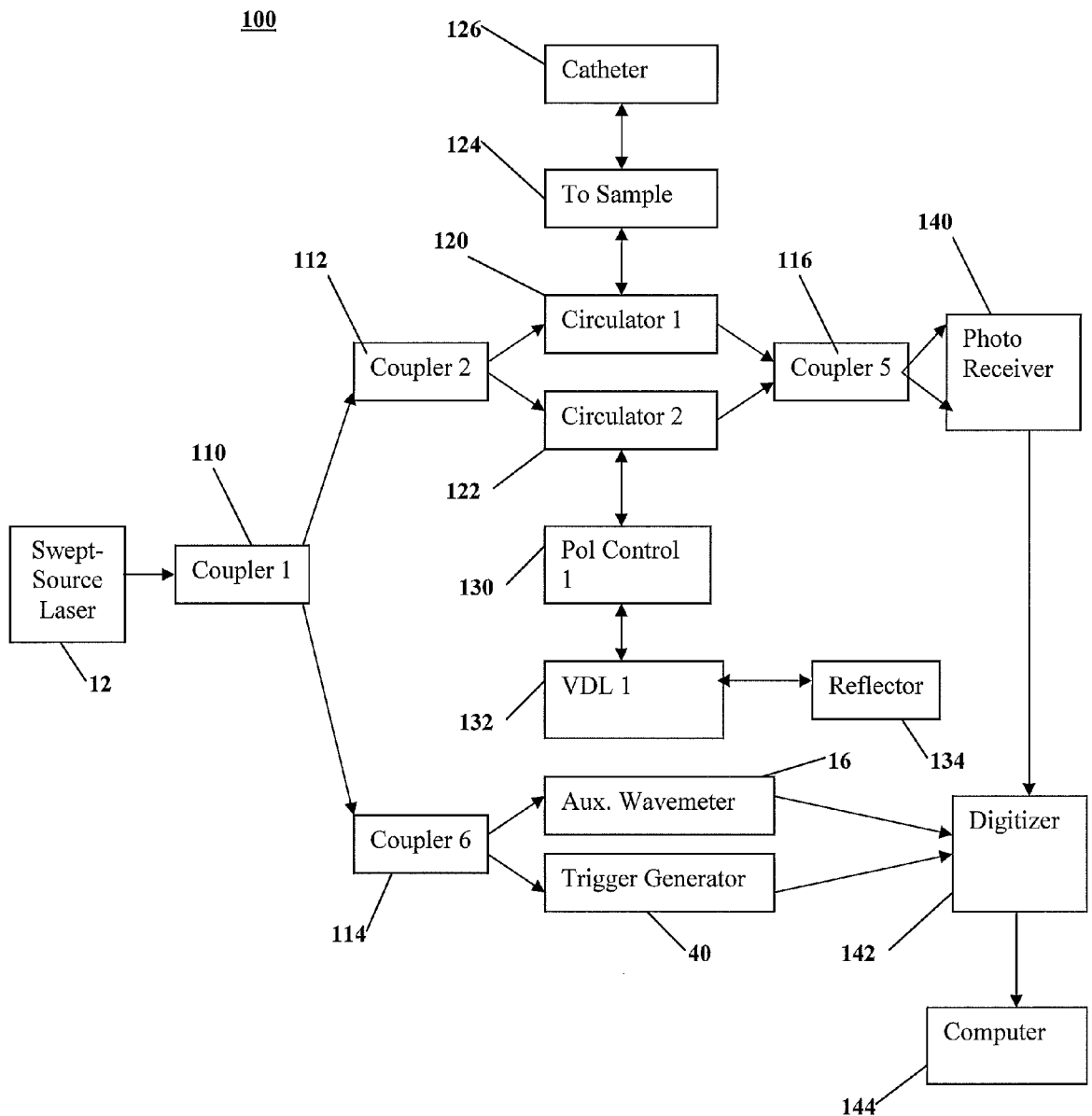
FIG. 8 is a schematic of one embodiment of the OCT interferometer.

In one embodiment, as shown in FIG. 8, the OCT interferometer 40 can comprise, a Mach-Zehnder interferometer configuration 100, which measures the complex mutual coherence function (magnitude and phase) between two non-reciprocal optical paths, one path encompassing an object under test, i.e. "the sample", and the other a reference path. Alternatively, the OCT interferometer can comprise a Michelson interferometer configuration which measures the same coherence function in a reciprocal configuration, i.e. the same splitter/coupler is used for both input splitting and output recombination. A SS-OCT system and calculations for the OCT interferometer is generally described and explained by the inventors in U.S. patent application Ser. No. 11/446,683, and Provisional Application Ser. No. 60/932,546, herein incorporated by reference.

The OCT system 100 has swept light source 12 with cascaded fiber optic couplers to subdivide the source light into three primary modules (1) the primary OCT interferometer, (2) the auxiliary wavemeter interferometer 16, and (3) the optical trigger generator 60. In one embodiment, the swept light source 12 is a High Speed Scanning Laser HSL-2000 (Santec) with an instantaneous coherence length of over 10 mm, an 110 nm Wavelength Scan Range, and a scan rate of 20 kHz. Line-arrows generally designate optical fibers coupled the elements of the OCT system 100.

As shown in FIG. 8, in one embodiment of the OCT interferometer 100, 90% of the radiant output of the swept light source 12 is split into the primary OCT interferometer by coupler 110. Coupler 110 splits light into a coupler 112 and a coupler 114. Then coupler 112 splits light 90% of the directed light to port 1 of a 3-port polarization insensitive optical circulator 120 for the sample path and 10% of the light is directed to port 1 of a 3-port polarization insensitive optical circulator 122 for the reference path. Port 2 of circulator 120 for the sample path is coupled to a sample 124. The sample path can be coupled to a probe or catheter 126 via a fiber optic rotary junction (not shown). Examples of a rotating catheter tip for the sample path include, a catheter for in-vivo imaging as described in U.S. Provisional Application No. 60/949,511, filed Jul. 12, 2007, a turbine-type catheter as described in Patent Cooperation Treaty application PCT/US04/12773 filed Apr. 23, 2004; or a rotating optical catheter tip as described in U.S. patent application Ser. No. 11/551,684; or a rotating catheter probe as described in U.S. patent application Ser. No. 11/551,684; each herein incorporated by reference for the methods, apparatuses and systems taught therein. The catheter can be located within a subject to allow light reflection off of subject tissues to obtain optical measurements, perform medical diagnosis, complete treatment, and the like.

Continuing with FIG. 8, port 2 of the optical circulator 122 is coupled to a polarization controller 130 and a Variable Delay Line ("VDL") 132 for the reference path. The VDL 132 extends to reference reflector 134. The variable delay line 132 system consists of an input fiber, a retro-reflecting mirror on a translation stage, and an output fiber. A dial controls the variable length, or delay, inserted into the optical reference path. The typical length variation is about 6 cm, while the typical time delay is about 300 picoseconds. The VDL 132 provides for larger path-length adjustments with micron-size adjustment being the smallest increments.

For the reference path, port 3 of the optical circulator 122 is then coupled to a 50/50 coupler 116, while port 3 of the optical circulator 120 is coupled to the coupler 116 for the sample path. The reference and sample paths encompass the total optical path beginning at the split in coupler 112, into ports 1 of the circulators 122 and 120, out of and back into ports 2 of the circulators 122 and 120, out of ports 3 of the circulators 122 and 120, and ending at their combination in coupler 116. The coupler 116 includes outputs 3 and 4 to a dual-balanced photoreceiver 140. The photoreceiver 140 comprise a detection element, such as an InGaAs photodiode and a transimpedance amplifier, which converts the electrical current signal generated by photons absorbed by the photo-detector element into a voltage signal that can be read by the digitizer. Typically, some gain amplification is given at this stage or in a following stage, as well as some filtering for removing noise that is outside of the relevant electrical signal bandwidth. The gained and filtered voltage signal is digitized. The OCT interferogram [S(k)] is digitized at 16-bit resolution using a high-speed PCI digitizer 142 board (AlazarTech ATS660, Toronto, Canada) coupled to the photoreceiver 140 from the primary OCT signal and the photoreceiver from auxiliary wavemeter 16. The external clock derived from the wavemeter and regenerated by the arbitrary waveform generator (Gage CompuGen) allows acquisition of OCT signal data directly in wavenumber (k) space. S(k) is converted using the Fast Fourier Transform (FFT) into the pathlength (z) domain. The magnitude of the transformed OCT A-scan [|S(z)|] represents the backscattered magnitude at depth z in the sample. The digitizer is coupled to a computer processor 144, which is a state-of-the-art workstation with a fast multi-core processor, RAID striped disk array, and large RAM space. Alternatively, the computer processor 144 includes a distributed acquisition and processing system, as described in U.S. patent application Ser. No. 11/868,334, filed Oct. 5, 2007, herein incorporated by reference.

OCT Depth Calibration and Automated Range Adjustment

Circular and cylindrical OCT scanning devices, i.e. the rotation catheter scanning devices discussed previously, sample physical space in an inherently polar coordinate system (e.g. radius and angle rather than length and width). Circular and cylindrical OCT scanning devices are applied to image physiological structures with cylindrical-like cross sections e.g., airways and blood vessel lumens). However, digital representations of the images (i.e. arrays of pixels representing numeric values) are inherently rectangular. A method for detecting and using OCT image features, either intentionally or artifactually generated, comprises automatically adjusting the depth range in polar ("radar-like") OCT images.

Polar OCT images must be converted from their rectangular representation before displaying to the viewer. Additionally, if quantitative values (e.g. lumen diameters, lumen areas, circumferences, etc.) are to be measured on the polar image, then the transformation from rectangular to polar must preserve relative distances between pixels in all dimensions (radial and angular). Generally, the OCT depth scan (y axis in rectangular coordinates) maps directly to radius and the OCT circumferential scan (x axis in rectangular coordinates) maps to some increment of 2*Pi radians (or 360°) polar angle.

For example: y=0 (the top row of the rectangular image) maps to radius=0 (the center of the polar image) and $y=y_{max}$ (the bottom row of the rectangular image) maps to radius=$y_{max}$ (the perimeter of the polar image). Likewise, x=0 (the left column in the rectangular image) maps to angle=0° and $x=x_{max}/2$ maps to approximately 180° and $x=x_{max}$ maps to an angle of approximately 359°.

For accurate quantitative dimensional measurement in polar images, pixels mapping to radius=0 must represent the actual physical space at the center of the axis of rotation of the imaging probe, otherwise the polar image will be artificially warped (expanded or contracted) in the radial direction. However, in an arbitrary OCT image, the pixels at y=0 do not necessarily satisfy this requirement and must be shifted in the y dimension until this is satisfied before mapping to a polar representation. Differential displacements (either controlled or uncontrolled) in the path length of the sample vs. reference arms of the interferometer will shift the pixels in the y dimension.

Uncontrollable displacements can occur when using cylindrical (actually helical)-scanning fiber-optic OCT catheters; for example, when the catheter is pushed or pulled longitudinally, the fiber-optic cable can be compressed or stretched and thus a path length displacement is incurred.

The method is an automatic recognition of the uncontrolled displacement effect based on searching for image features that should be stationary (but are not due to uncontrollable displacement), and successive calibration of OCT image data so that polar representations can then be used for accurate dimensional measurements. Finally, a method is provided for subsequent removal of image features in image prior to display.

Image features used by the method are generated within the catheter itself (not within the imaged subject or surroundings) and should appear somewhat stable in depth and consistent in intensity throughout the 360° rotation of the catheter. These include but are not limited to back reflections at interfaces between optical components (aka "ghost-lines" or "echo artifacts", these occur along the optical axis of rotating parts and thus appear as uniform circles in the polar image when no differential path length displacement occurs over the course of one catheter rotation), or reflections from the boundaries of or from within the stationary (non-rotating) catheter sheath (if it is circular in cross-sectional profile and also mechanically concentric with the rotating portion).

Steps in the automatic recognition and calibration method could include: (1) Averaging the OCT image frame along the x- (i.e. angular) dimension. This selectively enhances the feature(s) which are rotationally stable in the y dimension (i.e radius) vs. other image features generated by subject or surroundings. Efficacy of the method is improved if the image feature(s) used have high intensity relative to the surrounding pixels and if subject/environment features (noise) do not have strong circumferential symmetry; (2) Find feature(s) using peak searching, correlation, thresholding, or other pattern recognition algorithms known in the art. The efficacy of this method is improved if the range over which uncontrolled path length displacements can occur is known a priori, thus limiting the required search space; (3) Compare the y-value(s) of feature(s) found in step 2 to a pre-calibrated y-value which represents the actual physical location(s) of that feature(s) relative to the rotational axis, or to the location of a known "conjugate image" or "aliased image" of that feature(s) when using spectral-domain OCT; (4) Calibrate by shifting the OCT image pixels in the y dimension by the difference between searched feature(s) and pre-calibrated feature(s). Multiple features can be used to improve efficacy of the algorithm. After shifting the rectangular image in the y dimension, map to polar image coordinates. Radii measured to the center of the calibrated polar image will represent actual radii measured to the rotational axis in physical space. Often image features due to the catheter are unwanted for effective and distraction-free display of the subject/environment features. For example, the catheter image features could overlap the subject/environment features.

Steps to remove (or make less noticeable) the image features could include: (1) Cropping out the image feature(s) extent in the y/radial direction and in all columns/angles; (2) Calculating the average value of the pixels immediately inside and outside (above and below) of the cropped region for all columns/angles and inserting this averaged row/circumference in the cropped location. Unfortunately, the cropping operation can also remove subject/environment features and distorts the image in the radial dimension. This distortion makes measurement of accurate quantitative values on such images more complicated, because the measurement tool must then consider where pixels have and have not been cropped (or make the measurement on the un-cropped image).

Pathway 3: Auxiliary Wavemeter Coupled with an Analog Processor

Figure 9:
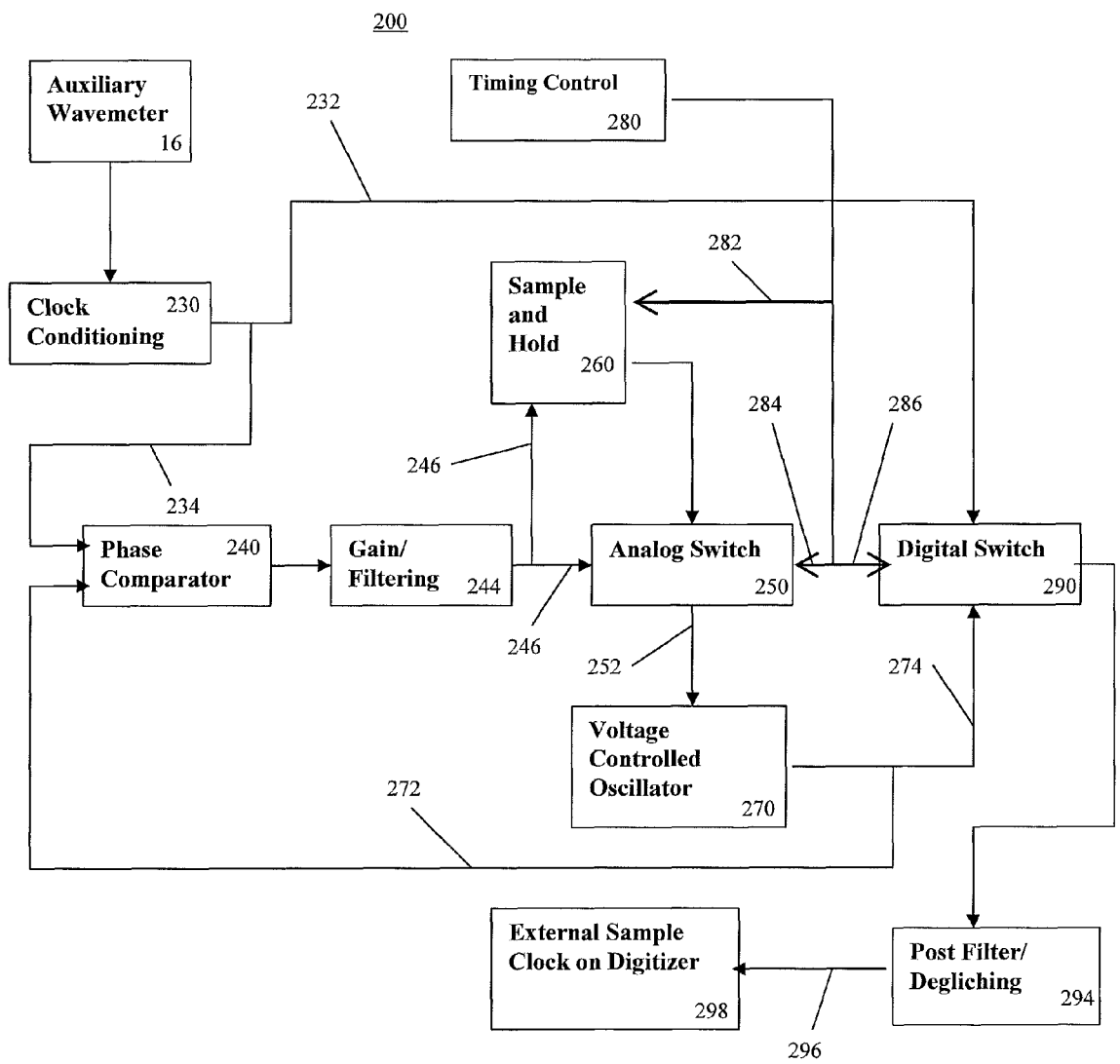
FIG. 9 is a schematic diagram of the circuit for direct external sample clocking of swept-source OCT using an optical wavemeter.

In another embodiment of the Uniform-Frequency Sample Clock 10, Pathway 3 comprises the auxiliary wavemeter 16 coupled with an analog processor, shown as in FIG. 1. The auxiliary wavemeter 16 can be any of the previously described wavemeters, Mach-Zehnder, Michelson, Fabry-Perot, inline Fabry-Perot, and the like. The analog processor can be any processor (e.g. filtering, pulse shaping, rectifying, and/or switching processor, etc.) that the wavemeter outputs to obtain a Uniform-Frequency Sample Clock signal which meets the specifications of the digitizer external clock input port. In one embodiment, the analog processor is a circuit 200 coupled to the high-speed digitizer to sample the clock signal, as shown in FIG. 9. During the laser sweep, this clock is the temporally-non-linear but the wavenumber-linear (frequency-linear) wavemeter clock. When the laser sweep is absent, this clock can be replaced with a dummy clock which has been pre-phase-locked with the k-space auxiliary wavemeter clock. Thus, high-speed digitizers are enabled to be operated in a mode where the Uniform-Frequency Sample Clock is used to directly sample the OCT signal, which avoids the need to acquire this Uniform-Frequency Sample Clock signal on a different channel and post-process data that slows down real time image display.

The sampling circuit 200 for the external sample clock signal is derived from the auxiliary wavemeter 16 during the limited duty cycle of a tunable laser source and is derived from a pre-locked (in phase and frequency) voltage controlled oscillator 270 ("VCO") during the non-sweeping segment of each duty cycle, as shown in FIG. 9. A VCO is an electronic oscillator designed to be controlled in oscillation frequency by a voltage input. The frequency of oscillation is varied by the applied DC voltage, while modulating signals may also be fed into the VCO to cause frequency modulation (FM) or phase modulation (PM); a VCO with digital pulse output may similarly have its repetition rate (FSK, PSK) or pulse width modulated (PWM). A phase locked loop (PLL) is used to sync the VCO output 274 with the optical wavemeter output before the sweep cycle is complete, at which time the external sample clock is switched from the optical wavemeter output to the output of the VCO (the dummy clock). A PLL is a control system that generates a signal that has a fixed relation to the phase of a "reference" signal. The PLL responds to both the frequency and the phase of the input signals, automatically raising or lowering the frequency of a controlled oscillator until it is matched to the reference in both frequency and phase. When the laser sweep begins again, lock is regained and the output is again switched to the k-space auxiliary wavemeter output.

The sampling circuit provides a continuous sample clock with acceptable jitter specifications to the digitizer's external sample clock input port. The locking of dummy and wavemeter clocks in phase and frequency by the PLL allows a handoff between clock sources to be free from spurious and instantaneous phase changes and frequency changes which could induce an error in the digitizer clock control circuitry.

In one embodiment, the sampling circuit 200 for direct external sampling of swept source OCT data comprises a clock conditioning block 230, a phase comparator 240, a gain-filtering block 244, a voltage controlled oscillator 270, a sample-and-hold block 260, an analog switch 250, a digital switch 290, a timing control block 280, and a post-filtering/deglitching block 294.

As shown in FIG. 9, the clock conditioning block 230 receives an input from the auxiliary wavemeter 16. The clock conditioning block 230 takes a sinusoidal analog voltage generated in the auxiliary wavemeter photodetector, and the clock conditioning block 230 filters out unwanted noise and DC component using a bandpass filter. The clock conditioning block 230 generates a digital pulse train (≈0-5V) at same frequency as input voltage signal and outputs 232 and 234 to the phase comparator 240 and main digital switch.

The phase comparator 240 outputs an analog voltage that is proportional to the difference in phase (and thus frequency) between the signals on its inputs, the conditioned k-space clock 230 and the VCO output 272. The phase comparator 240 can be embodied using various methods such as a charge-pump phase comparator, analog multiplier, an exclusive-NOR logic gate, i.e. an "XOR gate", etc. The phase comparator 240 outputs to the gain-filtering block 244. The gain-filtering block 244 averages the analog output voltage from the phase comparator 240 and is used to "tune" the PLL characteristics. The conditioned voltage output from the gain-filtering block 244 controls the VCO 270.

The voltage controlled oscillator 270 outputs a digital pulse train with frequency proportional to the input 252 voltage from the analog switch 250. The pulse train is negatively fed-back into an input 272 of the phase comparator 240. This closed-loop feedback or phase locked loop (PLL) causes the VCO 70 to oscillate in phase with the conditioned k-space clock 230. The phase locked loop syncs the VCO output 274 with the optical wavemeter output 16 before the sweep cycle is complete, at which time the external sample clock 298 is switched from the optical wavemeter output 16 to the output 274 of the VCO, dummy clock. When the laser begins to sweep again, lock is regained and the output is again switched to the k-space auxiliary wavemeter output 16.

The sample-and-hold circuit 260 samples and holds the output 246 voltage of the gain-filtering block 244 shortly before loss of the k-space auxiliary wavemeter clock 230. Then the sample-and-hold circuit 260 uses the analog switch 250 applied to the input 252 of the VCO 270. This maintains the VCO 270 output 272, 274 with the same phase and frequency as it was operating before loss of the k-space auxiliary wavemeter. Sample and hold operation is controlled from a signal 282 in the timing control block 280.

The analog switch 250 changes the input 52 to the VCO 270 between two analog sources (1) the sample-and-hold block 260, during dummy clock operation, and (2) the gain-filtering block 244 during wavemeter operation. The analog switch 250 is controlled from a signal 284 in the timing control block. The digital switch 290 changes the output of the entire clocking circuit between the digital conditioned auxiliary wavemeter clock 230 output 232 and the VCO 270 output 274 clock (when sweep is not present). The digital switch is controlled from a signal output 286 from the timing control block 280.

The timing control block 280 orchestrates analog switching 284, digital switching 286, and sample-and-hold operation 282 based on a trigger input signal from the swept laser source or other threshold detector. The post-filtering/deglitching block 294 removes any spurious glitches caused by switching, insures a strong full-range digital signal 296 is available for the digitizer external sample clock input.

Pathway 4: Auxiliary Wavemeter Coupled with an Analog Processor and D/A Converter In another embodiment of the Uniform-Frequency Sample Clock 10, Pathway 4 comprises the auxiliary wavemeter 16 coupled with the analog processor 20, the A/D digitizer 18, and a D/A converter 14, as shown in FIG. 1. Alternatively, a software processing step may be included after the D/A converter, or between the A/D digitizer and the D/A converter. The auxiliary wavemeter 16 can be any of the previously described wavemeters, Mach-Zehnder, Michelson, Fabry-Perot, inline Fabry-Perot, and the like. The analog processor 20 can be any processor (e.g. filtering, pulse shaping, rectifying, and/or switching processor, etc.) that the wavemeter 16 outputs to obtain a Uniform-Frequency Sample Clock signal, which meets the specifications of the digitizer external clock input port. In one embodiment, the analog processor 20 is the circuit 200 coupled to the high-speed digitizer to sample the clock signal, as shown in FIG. 9. During the laser sweep, this clock is the temporally-non-linear but wavenumber-linear (frequency-linear) wavemeter clock. When the laser sweep is absent, this clock can be replaced with a dummy clock which has been pre-phase-locked with the k-space auxiliary wavemeter clock. Thus, high-speed digitizers are enabled to be operated in a mode where the Uniform-Frequency Sample Clock is used to directly sample the OCT data signal, which avoids the need to acquire this Uniform-Frequency Sample Clock signal on a different channel and post-process data that slows down real time image display.

The analog processor 20 outputs to an A/D converter 18, which then outputs to the D/A converter. Alternatively, the software processing is included after the D/A converter, where the digitized signal is processed to a software clock signal that is input to the D/A converter, and then output to the External Clock input on the D/A converter. The D/A converter 14, is the arbitrary waveform generator, outputs the generated Uniform-Frequency Sample Clock signal for each laser sweep, triggered by an electrical synchronization pulse derived from the swept-source laser output. The external clock signal is derived from the analog processor 20 during the start-up calibration step, and then repeatedly outputted by the arbitrary waveform generator 14 for each subsequent optical trigger signal that occurs as the laser is sweeping. The Uniform Frequency Sample Clock signal is sent to the digitizer to allow the acquisition of data directly in wavenumber (k) space. From the auxiliary wavemeter, D/A converter, and then the A/D converter, and repeatedly generating the clock signal, the option of inserting a software processing step between the A/D and D/A steps remains.

Pathway 5: Auxiliary Wavemeter Coupled to the Swept-Source

In another embodiment of the Uniform Frequency Sample Clock 10, Pathway 5 includes coupling the swept source to the auxiliary wavemeter 16 and to the digitizer 32, without any pre-processing, as shown in FIG. 1. The auxiliary wavemeter 16 can be any of the previously described wavemeters, such as the Mach-Zehnder, Michelson, Fabry-Perot, inline Fabry-Perot, and the like. Alternatively, the auxiliary wavemeter 16 may be a Mach-Zenhder or Michelson interferometer depending on the OCT system employed. The auxiliary wavemeter 16 outputs a periodic signal uniformly spaced in wavenumber. The auxiliary wavemeter 16 output is used as an external clock for the High-Speed digitizer so that the OCT signal date is digitized uniformly in the wavenumber domain [S(k)]. Digitizing the OCT signal data uniformly in the wavenumber domain allows direct Fourier-transformation into the pathlength (z) domain and construction of the OCT image without time-intensive remapping. Following this approach, the nonlinear sweep characteristic of the tunable laser source is effectively removed and OCT images can be displayed in real-time.

Pathway 6: Auxiliary Wavemeter and Gas Cell Calibration coupled to Swept Source

Figure 10A:
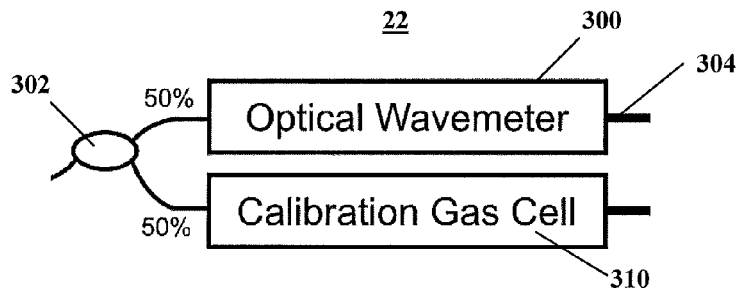
FIG. 10A is a schematic of a Calibration Gas Cell and the auxiliary wavemeter coupled from the swept source laser.

In another embodiment of the Uniform Frequency Sample Clock, Pathway 6 includes coupling the swept source 12 to the uniform frequency sample clock generator 22, as shown in FIG. 1. The uniform frequency sample clock generator 22 includes an optical wavemeter 300 and a gas cell calibration 310, as shown in FIG. 10A. A 50/50 coupler 302 splits the light from the swept source 12 to the optical wavemeter 300 and the gas cell calibration 310. The optical wavemeter 300 can be any of the previously described wavemeters, such as the Mach-Zehnder, Michelson, Fabry-Perot, inline Fabry-Perot, and the like. Alternatively, the optical wavemeter 300 may be a Mach-Zenhder or Michelson interferometer depending on the OCT system employed. The optical wavemeter 300 outputs a periodic signal uniformly spaced in wavenumber. The optical wavemeter output 304 is used as an external clock for the High-Speed digitizer so that the OCT signal data is digitized uniformly in the wavenumber domain [S(k)]. Digitizing the OCT signal data uniformly in the wavenumber domain allows direct Fourier-transformation into the pathlength (z) domain and construction of the OCT image without time-intensive remapping. Following this approach, the nonlinear sweep characteristic of the tunable laser source is effectively removed and OCT images can be displayed in real-time.

Figure 10B:
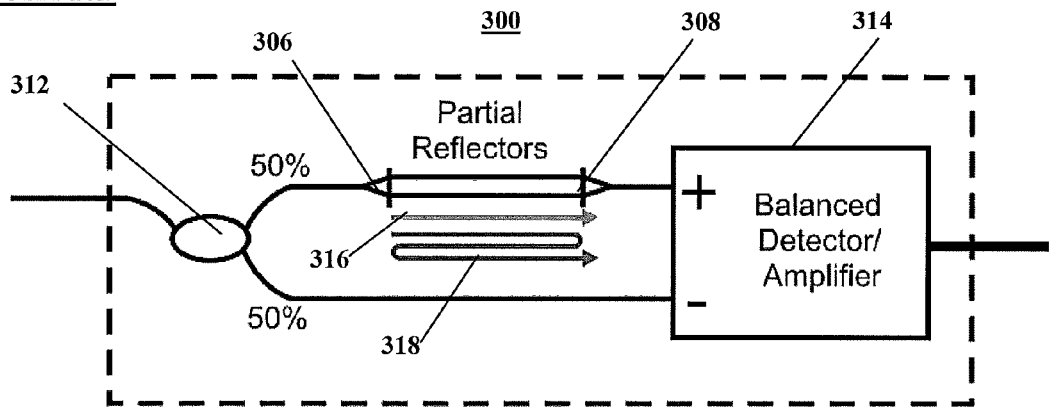
FIG. 10B is a schematic of the optical wavemeter where light making a single-pass 316 and a triple-pass 318 between partial reflectors interferes and produces a periodic signal uniformly spaced in wavenumber (k)

In one embodiment, the optical wavemeter 300 is a fiber-based Fabry-Perot interferometer with a pathlength difference generated by two in-line partially reflecting surfaces 306 and 308, as shown in FIG. 10B. A single-pass of light 316 and a triple-pass of light 318 between the partial reflectors 306 and 308 interferes and produces a periodic signal uniformly spaced in wavenumber (k). The pathlength difference is selected to produce a fringe output in wavenumber (k) space corresponding to Nyquist sampling of the longest detectable pathlength difference. The longest detectable pathlength can be a function of various factors and is always limited by the coherence length of the laser source. In cardiovascular applications, a fairly long detectable pathlength on the order of 10 mm may be applied. With swept laser sources, the pathlength can be as long as a few meters (2000 mm); however, the sweep may be very slow (10 sweeps/s). Sources with a longer coherence length (detectable pathlengths) that have a faster sweep speed, with a range of 2-2000 mm. Sources with very long coherence lengths can use multiplexing principles, as described in patent application entitled "OCT Using Spectrally Resolved Bandwidth, U.S. patent application Ser. No. 11/446,683. The Uniform Frequency Sample Clocking pathways are applicable to multiplexed OCT as well.

The partial reflecting surfaces 306 and 308 are encased in a mechanically and thermally isolated enclosure to insure phase stability. A 50/50 splitter 312 and parallel balanced detector 314 is incorporated in the optical wavemeter 300 to reduce noise and improve dynamic range, as shown in FIG. 10B. Harmonics generated by higher order passes between the surfaces are effectively suppressed by the cumulative reflectivity losses and roll-off due to the finite instantaneous coherence length of the laser source (10 mm). The output of the wavemeter 300 is electrically pre-filtered and amplified into a robust external clock for the high speed digitizer/analog-to-digital ("A/D") converter.

Figure 10C:
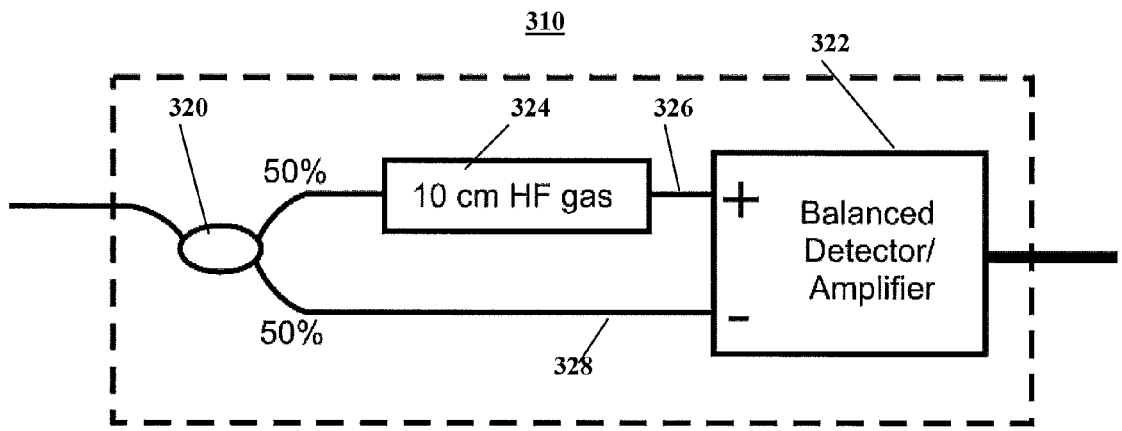
FIG. 10C is a schematic of the calibration gas cell.

As shown in FIG. 10C, the calibration gas cell 310 receives 50% of the light source from the coupler 302, where 50% of the light is split by a 50/50 coupler 320 to a balanced photo-detector/amplifier 322. In one embodiment, the calibration gas cell 310 includes a hydrogen fluoride ("HF") gas cell 324 (Wavelength References, Mulino, Oreg.) with a 10 mm pathlength and a calibrated absorption fingerprint in the 1250-1350 nm spectral range for the balanced detection scheme. Alternatively, other gas cells can be used as the calibration gas cell 310, with well known wavelength absorption bands and the pathlength selected according to the swept laser source. The well-known absorption fingerprint bands in the HF gas cell 324 result in a reduced detected intensity in the light transmitted through the gas cell 324, and as such provide a metric on the absolute lasing wavelength at those digitized sampling times. The sample number or sampling time scale can thus be converted to absolute wavelength at one or more samples, depending on the number of absorption lines. The detected wavemeter photocurrent signal 328 and the detected gas cell photocurrent signal 326 are combined in the digitizer to provide the relationship between the sample number or sampling time and lasing wavelength throughout the entire sweep. The detected photocurrent signal 326 from the gas cell is digitized concurrently with the OCT signal data and correlated with the known HF fingerprint to determine the wavenumber bias ($k_0$) of the swept source laser. Knowledge of wavenumber bias ($k_0$) allows accurate determination of the absolute wavenumber of each digitized sample throughout the spectral sweep, effectively removing any wavenumber offsets and/or phase instabilities in the laser source, wavemeter and sampling electronics.

The uniform-frequency sample clock signal which is based on the auxiliary wavemeter represents uniform intervals in wavenumber (k) biased by an unknown absolute wavenumber ($k_0$). Unfortunately, since the wavenumber bias ($k_0$) can vary between successive laser sweeps as a result of inherent instabilities in the tunable laser output spectrum, $k_0$ must be measured for each laser sweep for highly sensitive phase measurements. Gases with molecular absorption lines at NIST-calibrated wavenumbers provide unmatched stability and are used to calibrate optical spectra in a variety of high-precision spectroscopy applications.

Gas Cell Trigger

Figure 11:
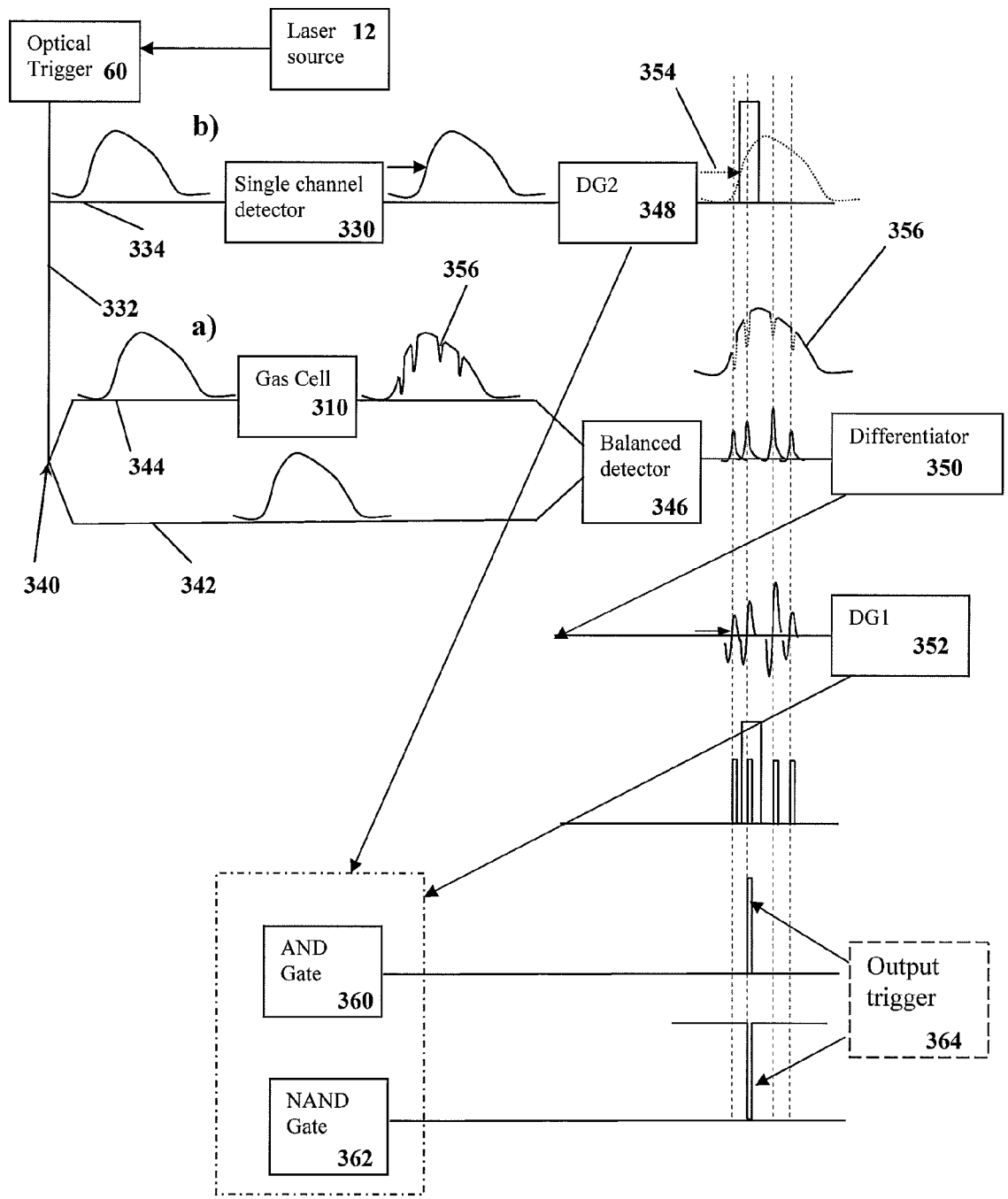
FIG. 11 is a schematic of one embodiment of Pathway 6.

As shown in FIG. 11, in another embodiment of the uniform frequency sample clock generator 22 includes coupling the laser swept source 12 to a single channel detector 330 and the gas cell 310. The laser swept source 12 power from the optical trigger 60 channel is divided into the gas cell channel 332 and a window channel 334 with the use of a coupler (not shown). The photocurrent of light passing through the gas cell 310 provides a more repeatable and stable optical trigger. An intensity-thresholded optical signal can suffer from variations in intensity of the laser while an absorption line in a gas cell does not vary and can provide a highly stable wavelength reference. The gas cell channel 332 and the window channel 334 propagate light simultaneously. The gas cell channel 332 may include >90% of the total trigger channel optical power. A coupler 340 is used to split the light into a reference channel 342 and a gas channel 344. In the gas channel 344, light passes through the gas cell 310 and a gas cell pulse 356 is outputted to one of the inputs of the balanced detector 346, while the reference light is directly outputted to the second input of the detector 346. The output voltage of the detector 346, which consists of pulses corresponding to the gas cell 310 absorption lines, is used as the input of a differentiator 350. The differentiator 350 is an electronic device where the output is the derivative of the input. For example, the differentiator may be a high pass filter. By differentiating the balanced detector 346 output, the maximums of the absorption lines are replaced with a zero crossing voltage. To produce the Transistor-Transistor Logic (TTL) pulses with rising edges corresponding to the central wavelength of the absorption gas cell 310 lines, a delay generator 352 (DG1) is coupled to the output of the differentiator 350. The level of voltage that used for generating the pulses should be several fold (by absolute value) above the RMS noise level to exceed the noise floor level and avoid generating pulses from noise. The time duration of the pulses should be at least several times less than distance between neighbor gas cell pulses. The time duration of the window pulse should be at least several times less than time between neighboring gas cell absorption line pulses to prevent false triggering (during one A-scan window pulse should be always overlapped with the only selected gas cell pulse).

The window channel 334 may include about 10% of the total power of the trigger channel. The light in the window channel 334 is detected with the single channel detector 330, so the shape of the detected voltage is repeating the shape of the laser sweep. The output of the single channel detector 330 is coupled to a delay generator 348 (DG2), which is used to produce a window pulse 354. The window pulse 354 is used to select one of the gas cell pulses 356 among others. The position during the sweep where the window pulse 354 starts is adjusted with the voltage level. The start position and width of the window pulse 354 are chosen so the window pulse 354 should totally cover one of the gas cell pulses 356. Since the gas cell pulse 356 is fixed in the wavenumber domain the window pulse 354 is jittering in the wavenumber domain from sweep to sweep. Therefore, width of the window pulse 354 should be several times wider than the selected gas cell pulse 356 width, so that the window pulse 354 covers the gas cell pulse 356 for every sweep. The window pulse 354 does not cover any of the neighboring gas cell pulses 356.

The outputs from DG1 352 and DG2 348 are used as input of a logical element AND gate 360 or NAND gate 362. The main condition for the logical element is its output when both inputs are high (logical 1) should be different from any other possible input logical states. The output of the logical element is the single TTL pulse with regulated width which is fixed at a specific wavelength and can be directly used as a gas cell trigger 364 for acquisition of the OCT signal data.

The gas cell trigger 364 is tightly connected with a reference wavelength, where the source of the reference wavelength is the gas cell 310. The gas cell 310 is a hermetic capsule containing a known gas, as describe previously. The central wavelength of absorption lines of the gas depend on molecular energy levels and practically do not depend on the external conditions such as temperature. If the swept laser source is centered at 1310 nm, then the gas cell 310 should have appropriate corresponding centered absorption lines. The need for the trigger 364 fixed at selected wavelength is a particular interest for phase sensitive OCT, where phase is determined as $$\varphi = kn\Delta z = \frac{2\pi n \Delta z}{\lambda},$$

where n is the refractive index, $\Delta z$ is the in pathlength difference between the sample and reference arms of OCT interferometer, $\lambda$ is the wavelength of light. Therefore, to have $\Delta\phi 32$ 0.1 at $\Delta z$=0.2 mm, the uncertainty of wavelength should be <10 pm. The sweep to sweep wavelength dependence of the swept source is several orders greater. Using the Pathway 6, the uncertainty is <2 pm for a 20 kHz scan rate of the swept source (with increasing swept source scan repetition rate the uncertainty of the trigger position increases linearly). Phase sensitive OCT provides additional contrast that may be color coded onto OCT intensity images.

Figure 12:
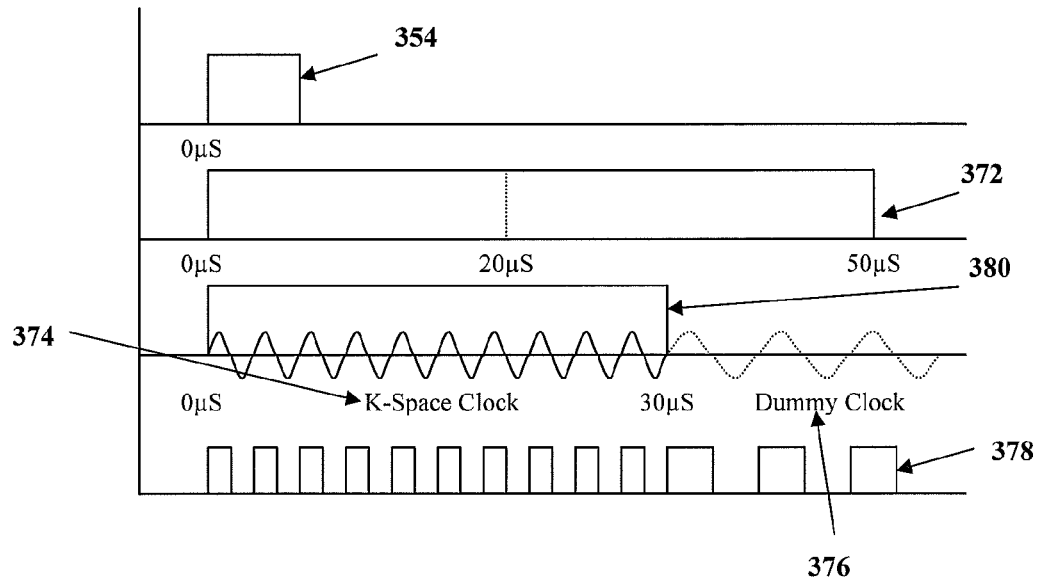
FIG. 12 is a graph schematic of one embodiment of external clock circuitry.

The gas cell trigger may be used for any OCT imaging system. The need for a trigger depends on the stability (instability) of the laser source. If the source is highly spectrally stable in time (i.e. the drive signal of the tuning element) then need for a gas cell trigger is less. Generally, the gas cell can provide a highly stable trigger. After the gas cell trigger 354 has been produced, the trigger 354 may be split into two signals. One signal is used to trigger the A/D digitizer card (Alazar) to start acquiring A-scans, and the other signal is directed to trigger the external clock circuitry 370, as shown in FIG. 12 The external clock circuitry 370 comprises a delay generator and a k-space/dummy clock switching circuit D. The delay generator comes first and uses an edge detect to sense when the differentiation circuit (trigger from the gas cell circuitry, 354) has gone high. After the edge has been detected, the delay generator outputs a 5V signal 372, where the time duration may be fixed using a resistor-capacitor combination. Time duration of the 5V pulse from the delay generator is selected to ensure sufficiently high signal to noise ratio of the K-space clock. In one embodiment, the delay generator can be programmed to provide a pulse duration from (20-50) μs. The 5V signal pulse 372 goes into the clock circuitry 370.

The clock circuitry 370 is composed of a buffer amplifier, a high pass filter, a switching network that can switch between a k-space 374 and a dummy clock 376, another high pass filter, and a comparator that converts the sine wave of the k-space 374 to a TTL signal 378. The resulting clock has a constant step in wavenumber space (k) during the (20-50) μs of the pulse duration from the delay generator 380 and constant duration in other time periods. The OCT data signal is acquired uniformly in wavenumber space 374 provided by the external clock circuitry 370.

As shown in FIG. 12, the original pulse from the gas cell circuitry 354 is used to produce the (20-50) μs pulse from delay generator 380 to be used to generate switching between k-space 374 and dummy clocks 378. The TTL pulse train 378 is produced from a sinusoidal signal and used as a final clock at the external clock input of the digitizer (ADC board).

Common Path OCT Interferometer

Figure 13:
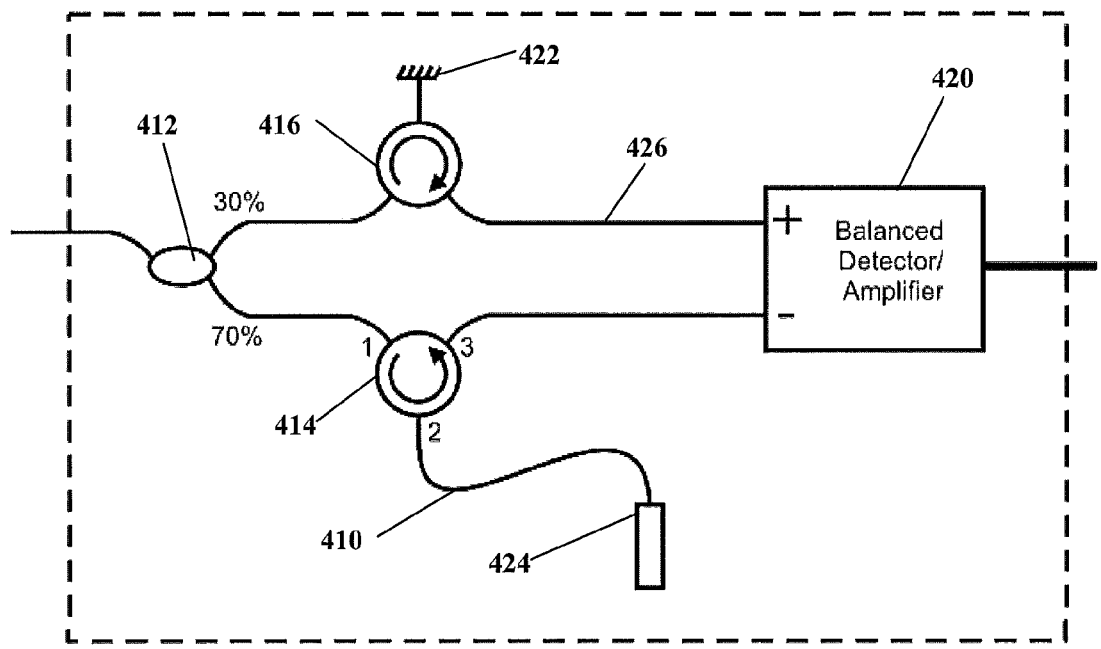
FIG. 13 is a schematic of common-path OCT interferometer in phase-sensitive Fourier Domain OCT.

In one embodiment, the OCT interferometer 40 is a common path interferometer 400, as shown in FIG. 13. The common path interferometer 400 comprises a Phase-Sensitive Fourier Domain OCT system 400 ("PS-FD-OCT") system wherein reference and sample light propagate in a common optical path 410. The common optical path 410 can propagate in an optical fiber, free space or some other material. Any environmentally induced perturbations in the common path experience common-mode rejection and phase-stable OCT signal data results. Some portion of the common optical path needs to be different, that is some portion of the sample path is distinct from the reference path. So while the reference and sample share some portion of the path, some portion of the sample path is distinct from the reference path.

As shown in FIG. 13, the optical layout of the common-path OCT interferometer employs a coupler 412 splitting light to a 3-port polarization-insensitive optical circulator 414 and a 3-port polarization-insensitive optical circulator 416. The circulator 414 includes a source light input on port 1, common reference and sample paths on port 2, and the output to a balanced photoreceiver 420 on port 3. Light is split (30%) to the circulator 416 from the input channel to a variable reflector 422 to reduce noise and improve detector dynamic range for the balancing channel 426 of the photoreceiver 420. The variable reflector 422 in the balancing channel insures equal power levels and spectral shape on the balanced detector's 420 two photodiodes. The distal end of the common-path fiber is terminated with a focusing gradient-index 424 (GRIN) lens. The GRIN lens 424 is optimized for <−65 dB return loss to minimize interference from spurious back-reflections, and may include a working distance of 5 mm and focused spot size of 20 um. A wedged 50% beam-splitter is aligned in the beam to provide a reference reflection. The sample may be positioned on two motorized linear translation stages and actuated in a raster pattern to create three-dimensional OCT volume scans. Alternatively, the sample path can be coupled to a scanning system with a flat and calibrated optical field. Such scanning systems are known in the art of optical design and can include for example a galvanometer, a scanning lens and field flattener lens. Alternatively, the sample path can be coupled to a probe or catheter via a fiber optic rotary junction. Examples of a catheter for in vivo imaging in the sample path include, U.S. Provisional Application No. 60/949,511, filed Jul. 12, 2007, a turbine-type catheter as described in Patent Cooperation Treaty application PCT/US04/12773 filed Apr. 23, 2004; or a rotating optical catheter tip as described in U.S. patent application Ser. No. 11/551,684; or a rotating catheter probe as described in U.S. patent application Ser. No. 11/551,684; each herein incorporated by reference for the methods, apparatuses and systems taught therein. The catheter can be located within a subject to allow light reflection off of subject tissues or nanoparticles to obtain optical measurements, medical diagnosis, treatment, and the like.

Figure 14:
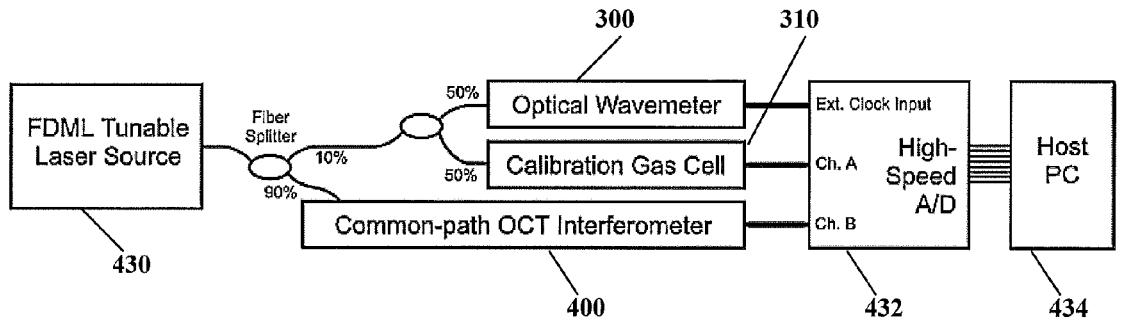
FIG. 14 is a block diagram of phase sensitive Fourier-domain OCT instrument with the Real-Time Imaging Clocking system.

As shown in FIG. 14, the common path OCT interferometer 400 is coupled to a FMDL tunable laser source 430, where the FMDL source 430 is coupled to the optical wavemeter 300 and the calibration gas cell 310. The OCT interferogram [S(k)] and calibration gas cell signature are digitized at 16-bit resolution on two channels of a high-speed PCI digitizer 432 board (AlazarTech ATS660, Toronto, Canada). The external clock derived from the wavemeter 300 output and allows acquisition of data directly in wavenumber (k) space. $S(k_0)$ is shifted to remove any bias as determined by the gas cell 310 absorption fingerprint and converted using the Fast Fourier Transform (FFT) into the pathlength (z) domain. The transformed OCT A-scan [S(z)] is a complex signal {|S(z)|, arg[S(z)]} representing the backscattered magnitude and phase at depth z in the sample. The digitizer 432 is coupled to a host PC 434 is a state-of-the-art workstation with a fast multi-core processor, RAID striped disk array, and large RAM space. The complex signal representing the A-scan may be used as input into an algorithm to solve the inverse problem to estimate the refractive index profile (n(z)) of the sample.

FIG. 15 compares axial point spread functions and OCT images generated with both uniform time sampling and the uniform frequency sample clocking approach 10 using the previously discussed Pathways. The graph shows the OCT point spread functions vs. depth for an internally clocked/remapped scheme 440 and the novel externally clocked scheme 442; the larger height and narrower width of the externally clocked functions results in greater signal-to-noise ratio ("SNR'), improved axial resolution, and suppressed artifacts, especially at larger depths (2.5 mm-3.5 mm). Additionally, the externally clocked scheme is less computationally and bandwidth intensive. Because most swept source lasers have a non-linear sweep rate (i.e. dv/dt≠constant), uniformly time-sampled fringe data produces a dispersion effect which results in sharp degradation of the point spread function (PSF) and reduced SNR with increasing scan depth, as shown in FIG. 15.

Multiple Uniform Frequency Clock Signals

Figure 18:
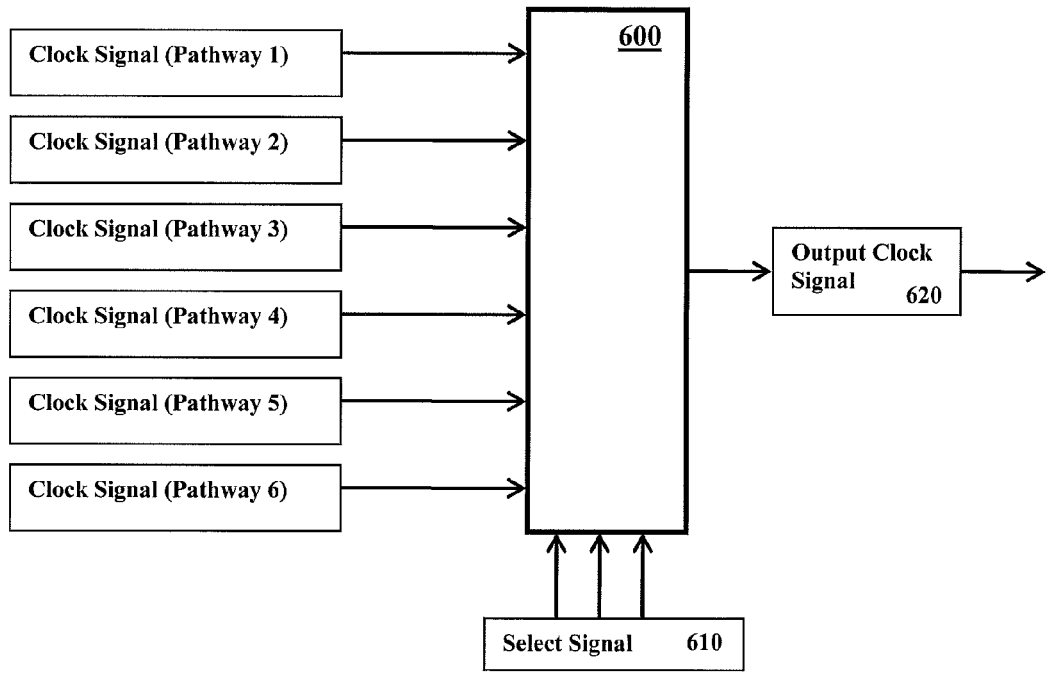
FIG. 18 is a schematic of the demultiplexer coupling multiple clock signals from various pathways.

For each acquisition channel, one clock signal may be active at a given time, which may be switched between different clock signals in any particular combination or order. Alternatively, more than one uniform frequency clock signal may be synchronously coupled to the ADC channel through a circuit that combines/alters the two clock signal to produce a synchronous signal that reveals something more than just one clock signal. As shown in FIG. 18, multiple clock signals from various pathways is inputted into a demultiplexer 600, where the demultiplexer has an input (possibly digital) that selects one of the input signals. The demulitiplexer would be applicable for the real time clock signal derived from the wavemeter and a backup clock signal is provided just in case the real-time circuitry fails or is intermittent in one way or another.

Phase Sensitive OCT System

Figure 16:
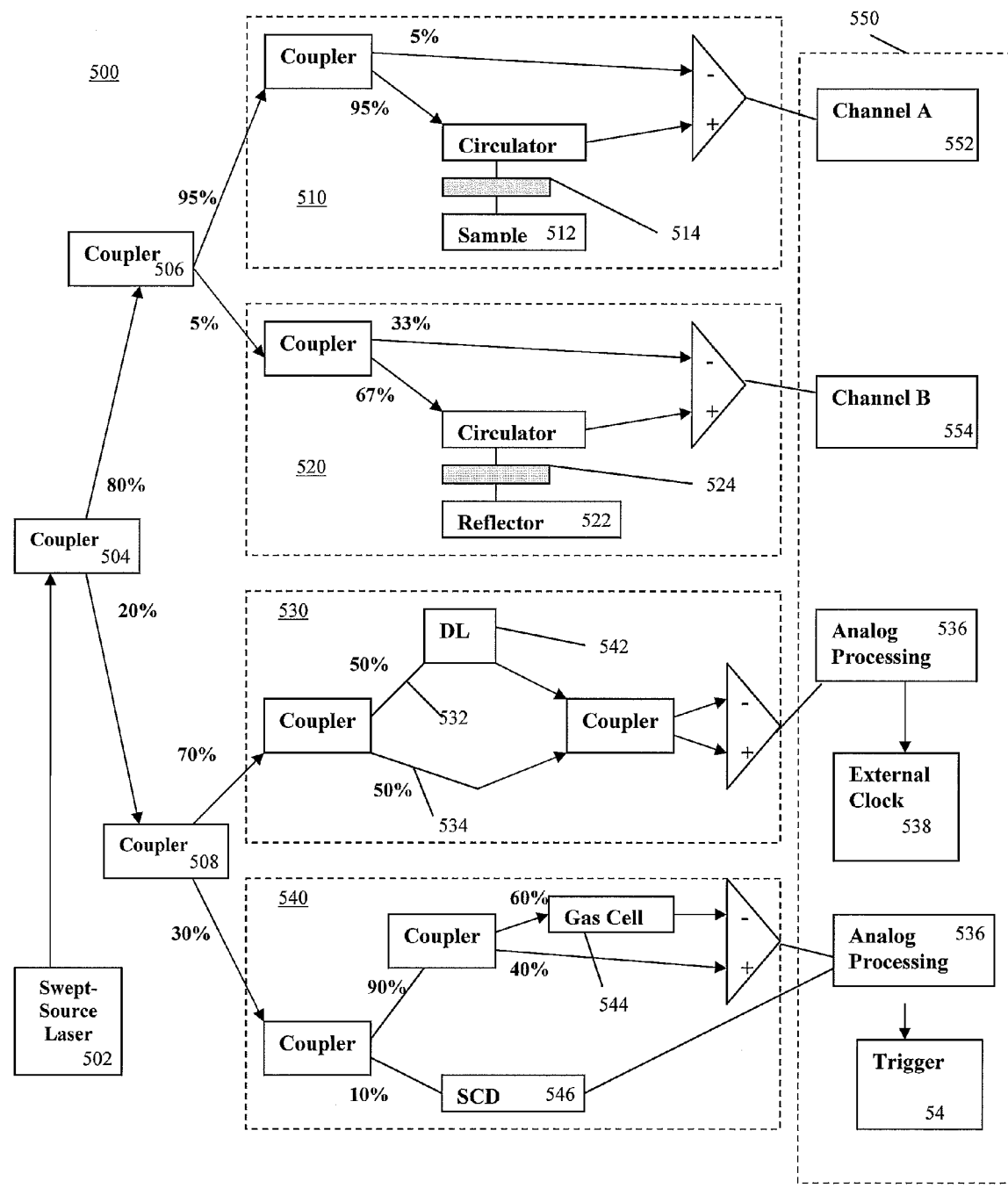
FIG. 16 is a schematic of one embodiment of the phase sensitive OCT interferometer configuration.

As shown in FIG. 16, an alternative Phase-Sensitive OCT (PS-OCT) system 500 comprising a signal interferometer 510, a reference interferometer 520, a clocking interferometer 530, a spectrally fixed trigger 540. The swept source laser 502 is coupled to an 80/20 splitter 504. The splitter 504 is coupled to a splitter 506 (95% transmittance, 5% reflection) and a splitter 508.

Light (λ=1310 nm, Δλ=100 nm, 20 KHz scan rate) emitted from a swept laser source 502 (Santec, Hackensack, N.J.) is input into four optical subsystems: the signal-interferometer 510; the reference-interferometer 520; the clocking-interferometer 530; and the spectrally fixed trigger 540. The sample under test 512 is positioned in the signal interferometer 510. Interference fringes ($\Gamma_s(v)$) are formed between light reflected from a splitter 514 and the sample 512 and directed into Channel A 552 of an analog-to-digital (A/D) converter 550 (ADC). The interference fringes ($\Gamma_r(v)$) in the reference interferometer 520 are formed analogously to $\Gamma_s(v)$ between light reflected from a splitter 524 and a high reflection mirror 522 and directed into Channel B 554 of the ADC 550. Interference fringes ($\Gamma_{cl}(v)$) in the clocking interferometer 530 are formed between light going through a first arm 532 and a second arm 534 of the Mach-Zehnder clocking interferometer 530, and after analogous bandpassing 536 served as a real time external clock 538 source for the ADC 550. The frequency of the external clock 538 depends on the optical path difference between 532 and 534 and varied with a variable Delay Line ("DL") 542. A sequence of the narrowband TTL like pulses are formed after light is outputted from a gas cell 544 (Wavelength Reference, Mulino, Oreg.) in the spectrally fixed trigger subsystem 540. The only pulse is selected using a time window produced out off a single channel detector ("SCD") 546 and serves as the spectrally fixed trigger for the ADC 550 at the AND gate using TTL pulse produced from laser sweep intensity profile.

Accuracy and sensitivity of the phase sensitive OCT instrument can be measured using a set of standardized metal films commonly used for calibrating resolution of atomic force microscopes. Sensitivity of the phase sensitive Fourier-domain OCT instrument is measured by placing a reflecting surface on a piezoelectric stepper (PolyTech PI, Auburn, Mass.) with 0.5 nm resolution. After aligning light reflection from the piezoelectric stepper, one-hundred A-scans are recorded for each position and the stepper is incremented 10 nm. Proceeding in this manner, accuracy and sensitivity of the phase sensitive Fourier-domain OCT instrument can be calibrated. Optical scanning systems that incorporate field flatteners can provide optical fields that are flat to within a fraction of a wave (e.g., 1/10 wave) a calibration procedure may be employed to correct residual phase variations that occur when scanning across the field. Calibration procedures using precision reference optical flats as reflective surfaces may be employed to correct for phase variation over the field curvature due to the scanning optics.

To achieve accurate and repeatable phase measurements, variations in spectral digitization and optical pathlength are minimized. The spectrally fixed trigger 540 provides a spectrally fixed trigger for each A-scan for the ADC 550. In the spectrally fixed trigger 540 system, 54% of the incident light is coupled into the negative channel of a balanced detector through a HF gas cell 544 (Wavelength Reference, HF-50) while 48% bypasses the gas cell and is directed into the positive channel of the balanced photoreceiver. The remaining 10% of incident light enters the single channel detector. Output of the balanced photoreceiver in the spectrally fixed trigger 540 consists of pulses corresponding to HF absorbance peaks that correspond to specific molecular energy levels with a fixed optical frequency. Using an analog electrical circuit, centers of the absorbance peaks are converted to zero crossings and produce short (0.3 µs) TTL pulses. One pulse is selected corresponding to the R(2) HF absorbance peak ($\lambda_{R2}$=1272.97030 nm) to serve as a scan trigger.

Although the spectrally fixed trigger 540 provides a stable spectrally fixed trigger for each A-scan, a one-clock period uncertainty exists in the first acquisition event for each A-scan due to lack of correlation between clock and trigger. In this case, a random phase jump can occur between successive A-scans and can be expressed as: $\Delta\phi_{jump}=2\Delta kn\Delta z_s=4\pi Rn\Delta z_s/(cf)$, where $\Delta k=2\pi R/(cf)$—wavenumber jump due to one-clock period uncertainty, $R=5.9 \cdot 10^{17}$ Hz/s—laser sweep rate, f=32.7 Mhz—clock frequency, $\Delta z_s$—distance from the splitter (SP1) to the probing depth in the sample. The reference-interferometer 520 is a reference interferometer and shares the same trigger and uniform-frequency optical clock with the signal interferometer 510 and thus experiences the same phase jumps as those in the signal interferometer 510 and is used to subtract phase jumps from the signal interferometer 510. Distance between the reflector 522 and the splitter 524 in the reference interferometer 520 $\Delta z_r$=2 mm matches the scan depth. The reference interferometer 520 signal is directed to channel B of the ADC 550 and processed in the same manner as the signal interferometer 510 data and used to calculate a phase free from jumps: $\phi_{ic}=\phi_{is}-\phi_r \cdot (n\Delta z_{is}/\Delta z_r)$, where $\phi_r$—phase in the reference interferometer calculated at $\Delta z_r$, i—depth pixel index, $\Delta z_{is}$—depth in the sample with index i, $\phi_{is}$—phase in the signal interferometer 510 at $\Delta z_{is}$. To avoid variations in pathlengths ($\Delta z_s$, $\Delta z_r$), all optical components forming interference fringes can be mounted on a common mechanical fixture.

The clocking interferometer 530 is a Mach-Zehnder fiber interferometer and provides the ADC 550 a uniform-frequency optical clock signal. The maximum clock frequency (35 MHz) is limited by the instantaneous coherence length ($L_{ic}$=12 mm) of the SS laser 502. When amplitude of the uniform-frequency optical clock falls below a threshold value a pseudo-clock is substituted. The pseudo-clock provides the ADC a clock signal to maintain un-interrupted operation. The uniform-frequency optical clock (f=32.7 MHz) preserves the original PSF and therefore high resolution and SNR through the entire scan depth $\Delta z_{max}$=3.8 mm in air, as shown in FIG. 15. The clocking interferometer 530 allows implementation of software for real-time display (39 frames/s for 512×400) of amplitude and phase M-Mode images.

Figure 17A:
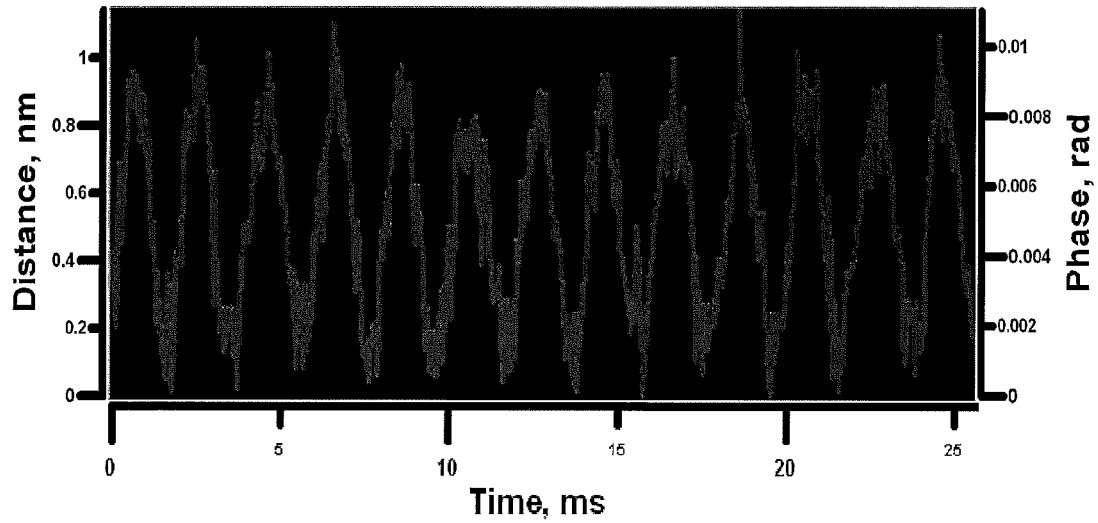
FIG. 17A-17C are graphs of the change in thickness in the piezofilm in response to application of a periodic voltage at increasing frequency (17A: 500 Hz, 17B: 1000H, 17C: 2000 Hz).
Figure 17B:
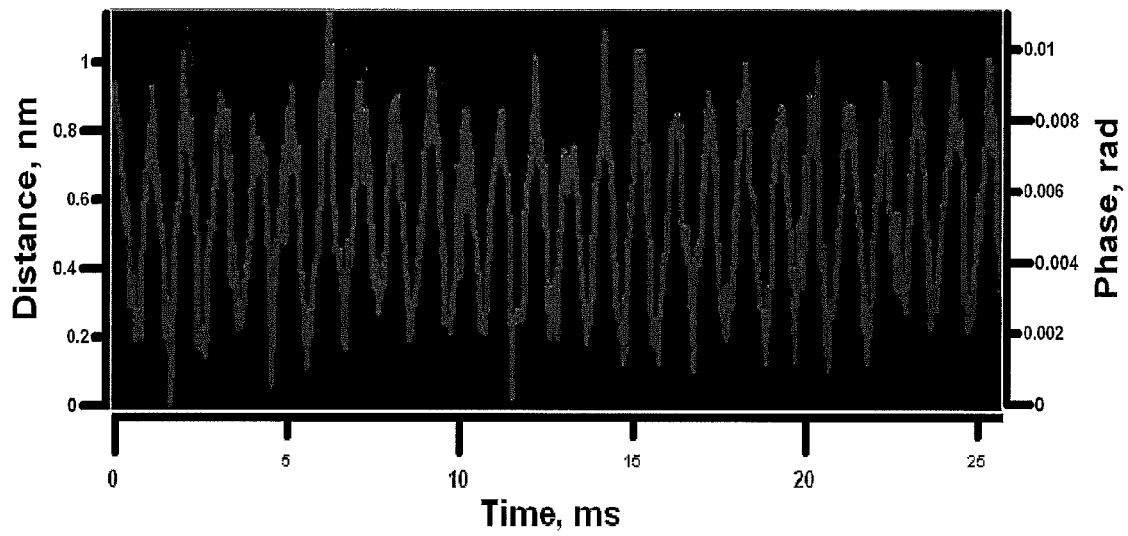
Figure 17C:
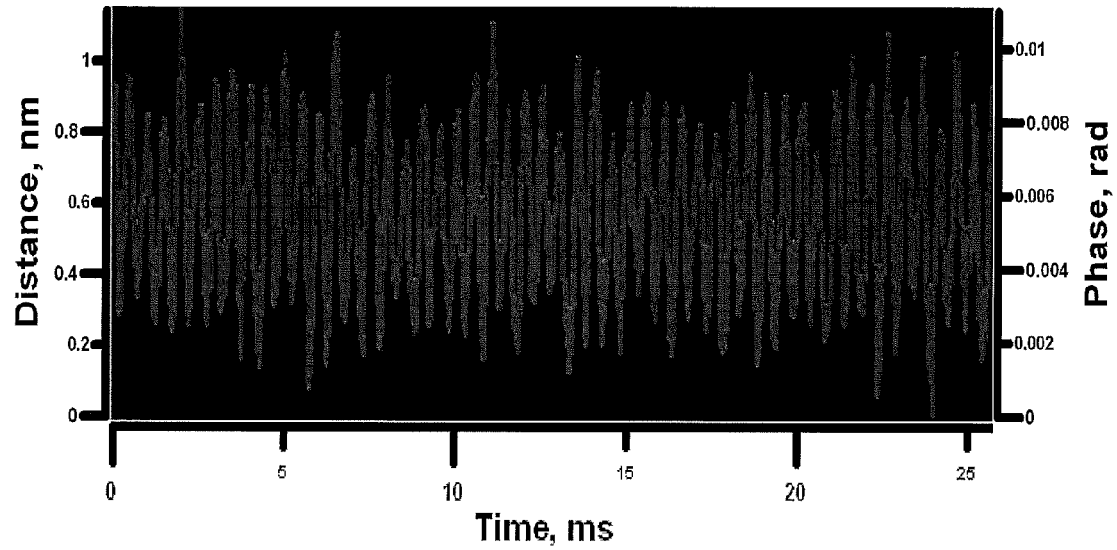

The strain constant of the PVDF copolymer piezofilm is $d_{33}=-38*10^{-12}$ m/V (Images SI Inc, Staten Island, N.Y.). A 10 V amplitude sinusoidal voltage to the piezofilm is applied using an Agilent function generator, which corresponds to 20 V peak peak change of voltage. The result change in the thickness of the piezofilm equals $d_{33}*20V$=0.76 nm. The voltage frequency was 500 Hz (FIG. 17A), 1000 Hz (FIG. 17B) and 2000 Hz (FIG. 17C).

The phase measurement versus time for the piezofilm induced by applied 10 V sinusoidal voltage with three different frequencies 500 Hz (17A), 1000 Hz (17B), 2000 Hz (17C). The measured phase (Y-scale on the right) is due to changing in thickness of the piezofilm. The phase ($\phi_{piezo}$) of light reflecting from the topmost surface of the PVDF copolymer piezofilm was measured with the PS-OCT system, converted to distance ($D_{piezo}=\lambda\phi_{piezo}/4\pi$) where $\lambda$—central wavelength of the Swept Source laser (nm), and compared with predicted values ($D_{theor}=d_{33} \cdot U$=760 pm). PS-OCT measurement of 1 kHz oscillations of the piezofilm is presented in FIG. 17C. In all three frequencies, good agreement was observed between experimental data and predicted values.

In measured displacement sensitivity (DS) versus scan depth, a reflecting mirror in the sample path of the signal interferometer 510 is placed at different distances from splitter 514. First, $DS=\phi_{SD}\lambda/(4\pi n)$ is measured and used in phase microscopy, where $\phi_{SD}$ is standard deviation (SD) of the phase at a fixed mirror position through a single M-scan, n=1. To estimate precision of DS, the procedure is repeated several times and calculate mean ±SD. The DS decreased from 65±3.7 pm at a depth of 280 µm to 325±16 pm at a depth of 1900 µm. Next, SNR-limited displacement sensitivity $DS_{SNR}$ was calculated, $DS_{SNR}=\lambda/(4\pi(SNR_s+(\Delta z_{is}/\Delta z_r)^2 \cdot SNR_r)^{1/2})$; where $SNR_s$ is SNR in the signal interferometer at mirror position $\Delta z_{is}$; $SNR_r$ is SNR in the reference interferometer at $\Delta z_r$. The mean ±SD for $DS_{SNR}$ was calculated from 5 A-scans. Displacement sensitivity at 280 µm is limited by SNR and the difference between DS and $DS_{SNR}$ at 380 µm is statistically insignificant, while for other depths difference between DS and $DS_{SNR}$ is statistically significant. This difference is attributed to variations in the start of each A-scan due to spectral jitter in the trigger from the spectrally fixed trigger 540. DS degradation was estimated with increasing scan depth due to uncertainty in the start wavelength ($DS_w$) by fitting the measured DS and $DS_{SNR}$ (first two points not included) with straight lines and subtracting the acquired $DS_{SNR}$ from DS. The calculated uncertainty for A-scan starting wavelength was $\Delta\lambda_{st}$=0.083 pm. Therefore, with sufficient SNR a DS of 19 pm may be obtained at a depth of 210 µm. Current SNR is limited by the ADC dynamic range and by number of digitizing events N=800 (SNR~$N^{1/2}$), which is limited by the clock frequency. The differential displacement sensitivity (DDS) relevant to Doppler blood flow measurements may be computed using the same approach as DS, but $\phi_{DDS}$-SD of the difference between to the expected value (DDS=√2DS) for phase measurements between independent successive A-scans.

The system-limited displacement sensitivity $DS_{TF}$ and differential displacement sensitivity $DDS_{TF}$ through scattering tissue phantoms using four cylindrical teflon tubes with a 1.6 nm inner diameter and different wall thicknesses was examined. The $DS_{TF}$ and $DDS_{TF}$ was measured from the inner surface of the teflon tubes ($n_{TF}$=1.35) in the same manner as for DS and DDS experiments using a single reflector. The teflon tubes were chosen since scattering properties are close to those in biological tissues and a cylindrical geometry introduces surface effects similar to those in blood vessels. Degradation of the sensitivity in both 179±4.3 pm (DS) and 234±9.5 pm (DDS) at a 127 µm tube thickness and down to 3670±270 pm (DS) 5000±410 pm (DDS) at 1300 µm tube thickness was observed. Sensitivities of 510±12.7 pm (DS) and 687±18.6 pm (DDS) at 407 µm and 713±12.4 pm (DS) and 992±18.9 pm (DDS) at 864 µm tube thicknesses were measured. This measurement of the OCT displacement sensitivity with increasing depth in scattering media and first PS OCT instrument can provide a DDS better than 1 nm in scattering media.

K-Space Clock Dispersion Correction

The difference in the dispersion between the reference path and the sample path is a common problem in OCT systems. The difference in dispersion between the reference and sample path can cause a degradation of the point spread function and reduce image quality. Mathematically, the point spread function S(x) is represented by Equation (1):

$$S(x)=\int F(k(t))e^{i\Delta\phi(k(t))}e^{ik(t)x}(dk/dt)dt+c.c., \qquad (1)$$

where S(x) is point spread function of the swept source OCT system from one sharp boundary; F(k(t)) is the power spectrum of the swept source laser; Re($e^{i\Delta\phi(k(t))}$)=D, is the dispersion mismatch component in the arms of OCT interferometer; dk/dt=C is the component due to non-uniform clocking in k-space; k is the wavenumber; t is time; and c.c. is the complex conjugate. Dispersion D can be altered, so D*C=1.

One method addressing the degradation of the point spread function is to account for the dispersion and apply a complex resampling algorithm to the raw data acquired from the Analog to Digital Converter (ADC). Another method comprises dispersion matching of the sample path to the k-space clock path with hardware dispersion matching. The k-space clock pathway is discussed previously. A hardware based approach comprises dispersion correcting the k-space clock to include the difference in dispersion between the sample and reference path. After the difference in dispersion has been measured, it is used to modify the k-space clock. If the OCT system is being clocked by an arbitrary waveform generator, a non-dispersion correct k-space clock signal is acquired by the ADC, the non-dispersion correct k-space clock signal is modified to take into account the difference in dispersion, and then this dispersion corrected k-space clock signal is used to clock the ADC to acquire the OCT data.

Alternatively, the method comprises modifying the k-space clock optics to account for the dispersion mismatch in the sample and reference path. The k-space clock optics includes some kind of interferometer that is relying on interference. The k-space clock corrective optical elements could include a glass window, fiber optic elements, a plurality of prisms, and/or a plurality of air gaps. By modifying the optics of the k-space clock then the effect of dispersion mismatch between reference and sample paths in the interferometer may be corrected. The dispersion corrected k-space clock optics enables the OCT system to be clocked with minimal dispersion in "real time", since the k-space clock would not require non-causal resampling techniques. The real time dispersion corrected clock could also be coupled with the arbitrary waveform generator pathway, where the difference is the real time dispersion correct k-space clock does not require dispersion resampling before being used.

The dispersion characteristic D is usually smooth and cosine modulated (D=Cos [$\Delta\phi(k(t))$]) versus k but C component can vary non-smoothly from digitized sample to digitized sample (neighbor k numbers).

The C component can vary from A-scan to A-scan. From the arbitrary waveform generator 50 (Gage CompuGen), the C component does not change from A-scan to A-scan. However, the dispersion component may still need correction from A-scan to A-scan in some embodiments of the arbitrary waveform generator.

Another approach addressing the degradation of the point spread function is the presence of an amplitude optical filter $\Phi(k(t))$ in the reference arm of interferometer, which converts Equation (1) to:

$$S(x)=\int F(k(t))e^{i\Delta\phi(k(t))}e^{ik(t)x}(dk/dt)\Phi(k(t))dt+cc. \qquad (2).$$

The amplitude optical filter $\Phi(k(t))$ facilitates to correct the distortion of the resolution with depth due to non-uniform k-space clocking (D*C*$\Phi$=1 may be easier to achieve than D*C=1). The depth resolution of the OCT system can be improved by effectively increasing the bandwidth of the power spectrum F(k(t)). Some power in the reference arm may be lost by damping central k-numbers and not modifying k-numbers at the edge of the spectrum.

All the Uniform Frequency Sample Clocking 10 Pathways, systems, and methods provide for external clocking of a swept laser source and can provide different Pathways, independently or in combination, to generate the clock, process the clock, and transmit the clock to the digitizer for uniform sampling of detected light in the wavenumber domain. Alternatively, all the Uniform Frequency Sample Clocking 10 Pathways may be combined with each other, in any particular combination or order. For example, an optical parameter of light can be measured by the clocking system and the optical parameter can be used in a model or look-up-table to predict the clocking wavenumber for a swept-source OCT system.

In one embodiment, the Uniform-Frequency Sample Clock Pathways for OCT systems image at least a portion of a sample. In one embodiment, the sample is a biological sample. The sample path of the OCT interferometers can be coupled to a probe or catheter via a fiber optic rotary junction to image a biological sample. The catheter can be located within a subject to allow light reflection off of subject tissues or nanoparticles to obtain optical measurements, medical diagnosis, treatment, and the like. In one embodiment, the Uniform-Frequency Sample Clock Pathways is coupled to OCT systems and catheters for imaging blood flow, such as in U.S. patent application Ser. No. 11/550,771, imaging a vessel or internal lumen of a patient, such as in U.S. patent application Ser. No. 11/446,683, and imaging nanoparticle labeled cells, such as in U.S. patent application Ser. No. 11/441,824, each herein incorporated by reference for the methods, apparatuses and systems taught therein.

While the embodiments have been described, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A clocking method for optical coherence tomography, comprising the steps of coupling a swept source to a uniform frequency sample clock pathway and characterizing the swept source, creating a digital representation of a clocking signal by the characterizing step, and generating the clocking signal as an output to a digitizer's external clock input to provide linear sampling for direct Fourier transformation into the pathlength domain.

2. The method of claim 1, further comprising outputting the clocking signal for each sweep to a digitizer triggered by an optical trigger generator separate from the swept source.

3. The method of claim 1, further comprising the step of outputting the clock signal for each sweep of the swept source triggered by an electrical synchronization pulse from the swept source output.

4. The method of claim 3, further comprising the step of providing at least one waveform to an arbitrary waveform generator, storing the waveform in the arbitrary waveform generator, and generating the waveform during a triggering event and coupling the waveform to the external clock input of the digitizer.

5. The method of claim 1, wherein the coupling step further comprises coupling an auxiliary wavemeter to the swept source and processing an output of the auxiliary wavemeter to generate the clocking signal.

6. The method of claim 5, further comprising the step of outputting the clock signal for each sweep of the swept source triggered by an electrical synchronization pulse from the swept source output.

7. The method of claim 6, wherein the processing step further comprises a digital processing step.

8. The method of claim 6, further comprising the step of repeatedly outputting the digitally-processed signal by an arbitrary waveform generator.

9. The method of claim 8, further comprising the step of collecting an intensity profile of the sweep with a sweep detector, shaping the intensity profile with a delay generator, and coupling the shaped intensity profile to a switching circuit.

10. The method of claim 9, further comprising the step of coupling the auxiliary wavemeter output to the switching circuit and outputting the clock signal from the electronic switching circuit under a first condition.

11. The method of claim 5, wherein the processing step is an analog processing step.

12. The method of claim 11, further comprising the step of coupling the auxiliary wavemeter to a sampling circuit during the limited duty cycle of the swept source and deriving the clock signal from a pre-locked voltage controlled oscillator during the non-sweeping segment of each duty cycle.

13. The method of claim 4, wherein the processing step further comprises an analog processing step further comprising coupling the analog processing output to a digitizer, coupling the digitizer output to digital to analog processor to generate the clock signal.

14. The method of claim 1, wherein coupling step further comprises the steps of coupling the swept source to a uniform frequency sample clock generator and generate the clocking signal.

15. The method of claim 14, wherein the uniform frequency sample clock generator further comprises a gas cell providing a metric on the absolute output wavelength at digitized sampling times and an optical wavemeter coupled to a digitizer providing the relationship between the sampling time and output wavelength, further comprising determining the wavenumber bias of the swept source.

16. The method of claim 14, wherein the uniform frequency sample clock generator further comprises a detector channel and a gas cell channel to generate a gas cell pulse, differentiating the gas cell pulse to replace the maximum absorption gas cell lines with a zero crossing voltage, producing a transistor-transistor logic pulse with rising edges corresponding to the central wavelength of the absorption gas cell lines, repeatedly outputting the shape of the source sweep, and producing a window pulse to select one of the gas cell pulses.

17. A system for uniform frequency sample clocking comprising:
   a sampling circuit including an external sample clock signal from an auxiliary wavemeter during the limited duty cycle of a tunable source and a pre-locked voltage controlled oscillator during the non-sweeping segment of each duty cycle including a locked voltage;
   a phase locked loop to sync the voltage controlled oscillator output with the auxiliary wavemeter output, at which time the external sample clock is switched from the optical wavemeter output to the output of the voltage controlled oscillator, wherein the locked voltage is regained when the swept source begins to sweep and the output is switched to a k-space auxiliary wavemeter output.

18. An optical coherence tomographic system comprising: a swept light source including a plurality of fiber optic couplers to subdivide the swept light source into a primary optical coherence tomographic interferometer, and a uniform frequency sample clock pathway to generate a clock signal allowing an acquisition of the optical coherence tomographic signal data directly in the wavenumber (k) space, wherein the uniform frequency sample clock pathway comprises an auxiliary wavemeter, and an optical trigger generator;
   a digitizer coupled to the photoreceiver from the primary optical coherence tomographic interferometer and the photoreceiver from the auxiliary wavemeter; wherein the external clock derived from the auxiliary wavemeter is regenerated by an arbitrary waveform generator to allow the acquisition of optical coherence tomographic signal data directly in the wavenumber (k) space.

19. An optical coherence tomographic system comprising: a swept light source including a plurality of fiber optic couplers to subdivide the swept light source into a primary optical coherence tomographic interferometer, and a uniform frequency sample clock pathway to generate a clock signal allowing an acquisition of the optical coherence tomographic signal data directly in the wavenumber (k) space, wherein the uniform frequency sample clock pathway comprises a signal interferometer, a reference interferometer, a clocking interferometer, and a spectrally fixed trigger,
   the interference fringe of the single interferometer and the interference fringe of the reference interferometer are coupled to a digitizer;
   the interference fringe of the clocking interferometer is coupled to an analog processor to serve as the external clock signal; and
   spectrally fixed trigger includes a gas cell and single detector, wherein the gas cell forms at least one narrowband TTL pulse and the pulse is selected using a time window produced by the single channel detector to serve as the spectrally fixed trigger for the digitizer.

* * * * *